United States Patent [19]

Cheikh

[11] Patent Number: 5,616,123
[45] Date of Patent: Apr. 1, 1997

[54] DELIVERY OF SOLID DRUG COMPOSITIONS

[75] Inventor: Roland C. Cheikh, Issy-Les-Moulineaux, France

[73] Assignee: Delab, Paris, France

[21] Appl. No.: 460,545

[22] Filed: Jun. 2, 1995

Related U.S. Application Data

[63] Continuation of Ser. No. 300,713, Sep. 2, 1994.

[51] Int. Cl.$^6$ ................................................. A61M 31/00
[52] U.S. Cl. ........................ 604/60; 604/51; 604/57; 604/93
[58] Field of Search ..................... 604/60, 27, 28, 604/48, 51, 52, 53, 57, 64, 93, 131, 154, 174, 179, 246, 59, 63; 128/DIG. 12, DIG. 1

[56] References Cited

U.S. PATENT DOCUMENTS

| | | |
|---|---|---|
| 2,513,014 | 6/1950 | Fields . |
| 3,760,806 | 9/1973 | Leeper . |
| 3,995,631 | 12/1976 | Higuchi et al. . |
| 3,995,632 | 12/1976 | Nakano et al. . |
| 4,086,914 | 5/1978 | Moore . |
| 4,093,708 | 6/1978 | Zaffaroni et al. . |
| 4,177,256 | 12/1979 | Michaels et al. . |
| 4,263,910 | 4/1981 | Pardekooper et al. . |
| 4,313,439 | 2/1982 | Babb et al. ................ 604/28 X |
| 4,327,725 | 5/1982 | Cortese et al. . |
| 4,340,054 | 7/1982 | Michaels . |
| 4,342,312 | 8/1982 | Whitney et al. ............ 604/51 X |
| 4,525,164 | 6/1985 | Loeb et al. . |
| 4,529,401 | 7/1985 | Leslie et al. ................ 604/131 |
| 4,595,583 | 7/1986 | Eckenhoff et al. . |
| 4,620,848 | 11/1986 | Sutherland et al. ........... 604/154 |
| 4,655,766 | 4/1987 | Theeuwes et al. . |
| 4,685,903 | 8/1987 | Cable et al. ................. 604/154 |
| 4,711,251 | 12/1987 | Stokes . |
| 4,720,384 | 1/1988 | Di Luccio et al. . |
| 4,723,958 | 2/1988 | Pope et al. . |
| 4,753,636 | 6/1988 | Free . |
| 4,834,704 | 5/1989 | Reinicke . |
| 4,888,074 | 12/1989 | Pocknell . |
| 4,900,304 | 2/1990 | Fujioka et al. . |
| 4,936,827 | 6/1990 | Grimm et al. . |
| 4,941,874 | 7/1990 | Sandow et al. . |
| 4,976,966 | 12/1990 | Theeuwes et al. . |
| 4,994,028 | 2/1991 | Leonard et al. . |
| 5,030,216 | 7/1991 | Theeuwes et al. . |
| 5,086,787 | 2/1992 | Grandjean et al. . |
| 5,226,895 | 7/1993 | Harris . |

FOREIGN PATENT DOCUMENTS

| | | |
|---|---|---|
| 0139286A2 | 5/1988 | European Pat. Off. . |
| 0292936A2 | 11/1988 | European Pat. Off. . |
| WO93/23017 | 11/1993 | WIPO . |

*Primary Examiner*—Corrine M. McDermott
*Assistant Examiner*—N. Kent Gring

[57] ABSTRACT

A method of parenterally administering a drug to a patient for immediate dispersal of the drug once administered by obtaining an anhydrous, solid drug composition consisting essentially of the drug and up to 50%, by weight, of a pharmaceutically acceptable carrier, wherein the drug and the carrier are selected and compounded such that the drug is dispersed from the composition upon contact with parenteral fluids and is distributed within the patient's bloodstream according to a blood level profile of the drug that is comparable to a blood level profile of the drug when administered in a liquid formulation, and introducing the solid drug composition into parenteral fluids of the patient.

8 Claims, 17 Drawing Sheets

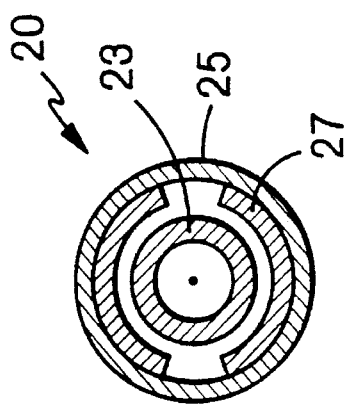
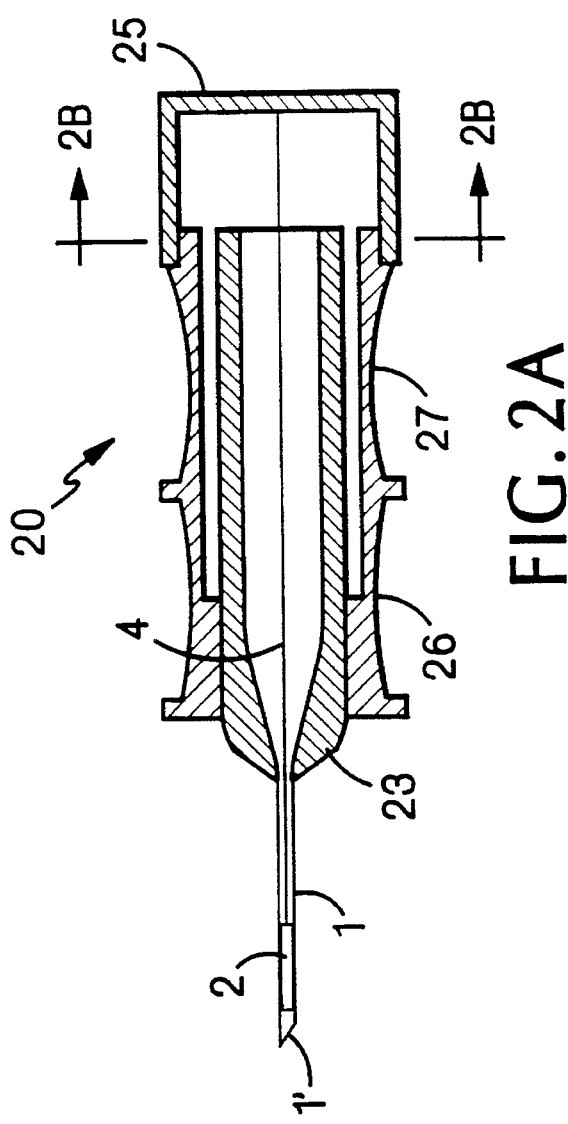
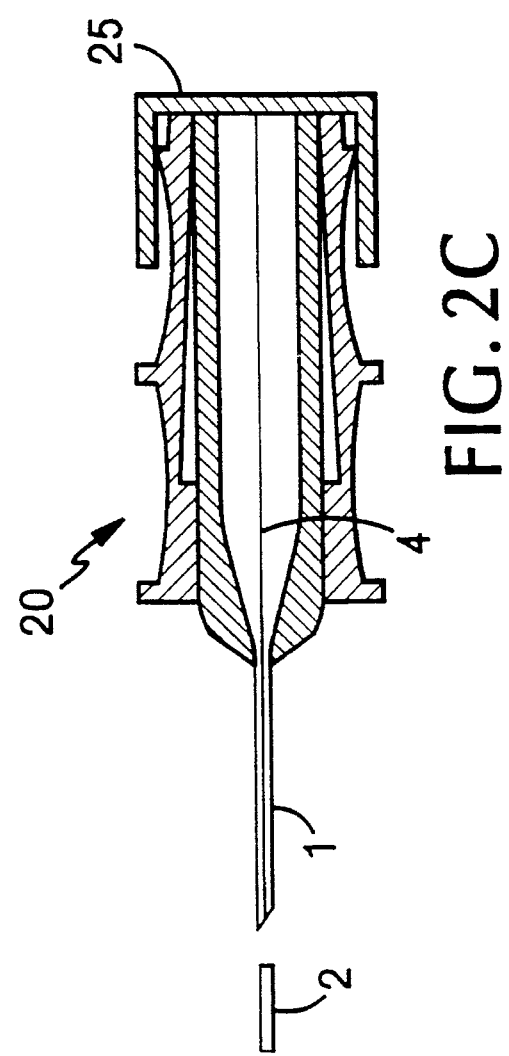

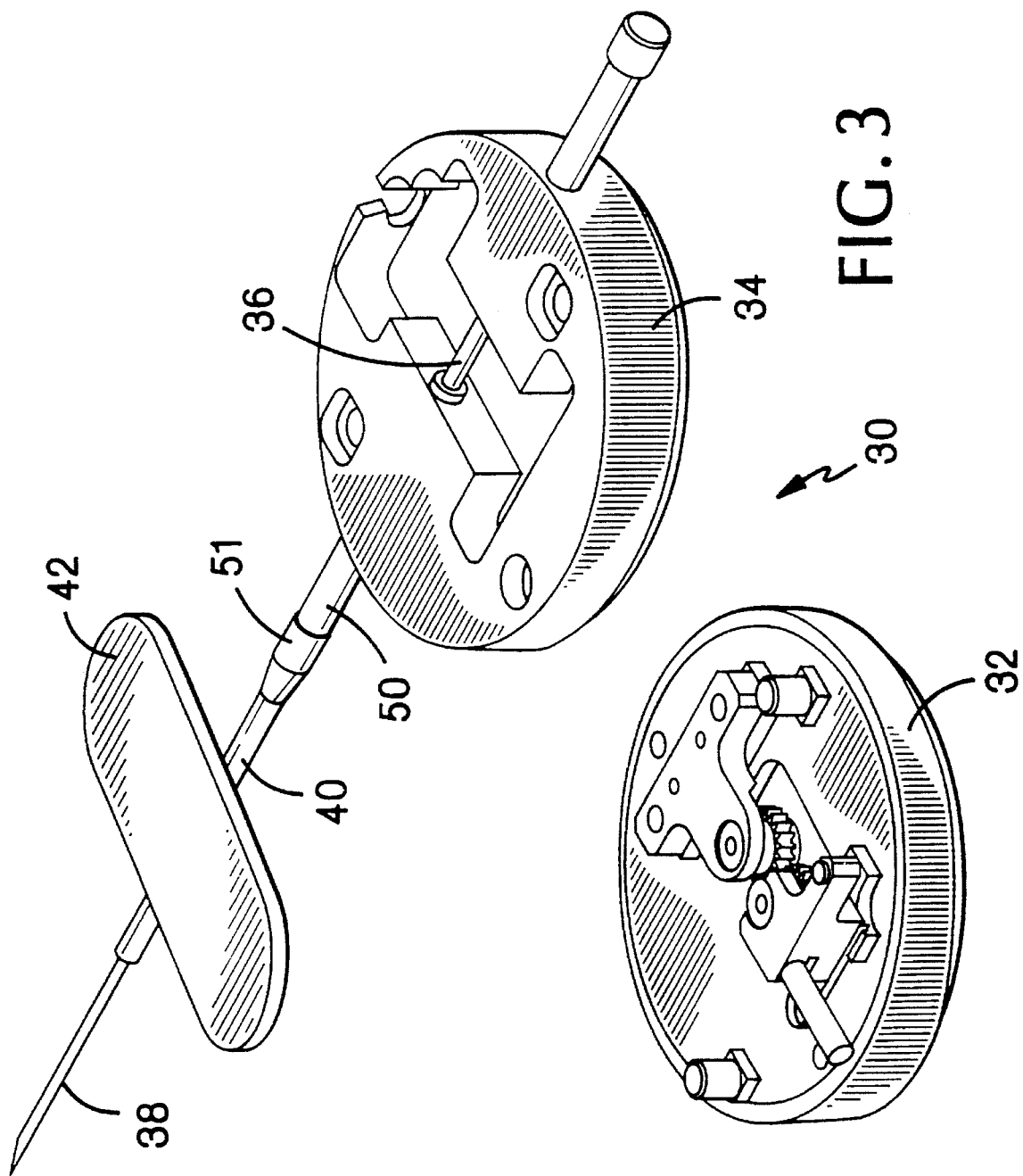

DELIVERY OF SOLID DRUG COMPOSITIONS

This is a continuation of application Ser. No. 08/300,713, filed Sep. 2, 1994 now pending.

BACKGROUND OF THE INVENTION

This invention relates to the parenteral administration of solid drug compositions.

Drugs are administered parenterally, e.g., by injection of drug solutions, for various reasons. For example, injection, rather than oral administration, is used for compounds which partially or totally degrade in the gastrointestinal tract. Injections are also preferred when a rapid response is required, i.e., where the time lag between oral administration of the drug and its action on the target site is too long. In addition, the effective use of drugs often requires continuous, controlled parenteral administration to achieve the desired effect. This type of prolonged parenteral administration also has been achieved by the injection of drug solutions.

The continuous parenteral delivery of drugs can be accomplished by mechanical perfusion devices that include a catheter and needle, or by sustained release compositions that typically include a drug and a carrier such as polylactide polymers that retards the release of the drug so that it is slowly dispensed over time. See, e.g., Boswell et al., U.S. Pat. No. 3,773,919, and Hutchinson, U.S. Pat. No. 5,004,602.

Perfusion devices include wearable devices that are powered by electrical or mechanical force. Such devices are generally quite large, often being between 40 cm$^3$ and 1000 cm$^3$ in volume. As a result, these devices may cause physical inconvenience to the patient. Electrically powered devices can be designed to be reused upon changing the catheter and needle after each use, whereas mechanically powered devices are generally designed to be disposable.

Electrically powered pumps include syringe pumps, in which a mechanical screw depresses a plunger on a syringe, and peristaltic pumps, in which a rotating wheel exerts pressure on a tube to inject a liquid drug solution into a patient. Piezoelectric pumps have also been used to inject small quantities of liquid drug solutions into patients. Mechanically powered wearable pumps are powered by osmotic pressure, gas or air pressure, or mechanical spring forces.

Although the injection of liquid drug solutions offers certain advantages, the liquid solutions used for injection are associated with a number of disadvantages that arise from the use of necessarily large volumes of liquid excipients. For a normal injection, e.g., by syringe and needle, the drug to be administered must be soluble or capable of suspension in water or other therapeutically acceptable liquid excipient. However, a significant volume of liquid is often needed for the suspension or dissolution of even a small amount of an active drug compound. For example, weight ratios of drug to excipient of 1:100 or even 1:1000 are used. This large volume can make injections uncomfortable or even painful to a patient, especially for patients who are required to have an injection at least once a day for months or even a lifetime, e.g., diabetics who require one or two daily injections of insulin. In addition, drugs are often less stable when mixed into excipient solutions, and the extemporaneous reconstitution of a sterile solution is always associated with an inherent risk of contamination.

SUMMARY OF THE INVENTION

The invention is based on the discovery that any drug can be formulated as an anhydrous, solid composition that nevertheless allows for immediate delivery of the drug once injected into the bodily fluids. The new drug compositions reduce the volume of known liquid drug solutions by hundreds to thousands of times. Thus, the invention features systems for the injection of solid drug compositions, e.g., as a single dose bolus from pre-loaded needles with a disposable syringe-like device or an external wearable pump device, that solve many of the inadequacies of existing parenteral liquid drug delivery systems.

The syringe-like device is inexpensive, and can be manufactured using existing elements of standard syringes. The external pump provides a slow injection of the solid drug composition, and can also be manufactured from many standard elements.

The present system provides the added benefit that once a pre-loaded needle is used, either in the syringe-like device or in the external pump, the needle cannot be reloaded by a patient, and the syringe or pump cannot be used to deliver liquid drug formulations. Thus, the system is much safer than standard liquid drug delivery syringes, which can be potentially reused, transmitting disease such as AIDS or hepatitis.

In addition, the system is easy to use since it requires no extemporaneous preparation of the drug composition, and no special skill to properly inject the drug composition, e.g., no need to find and inject the drug composition into a blood vessel. Therefore, the drug composition need not be administered by a specialist.

In general, the invention features a method of parenterally administering a drug to a patient, e.g., an animal or human patient, for immediate dispersal of the drug once administered, by (1) obtaining an anhydrous, solid drug composition consisting essentially of the drug, e.g., a peptide or protein, and up to 50%, by weight, of a pharmaceutically acceptable carrier, e.g., a water-soluble, water miscible, or otherwise biologically dispersible carrier, wherein the drug and the carrier are selected and compounded such that the drug is dispersed from the composition upon contact with parenteral fluids and is distributed within the patient's bloodstream according to a blood level profile of the drug that is comparable to a blood level profile of the drug when administered in a liquid formulation, and (2) introducing the solid drug composition into parenteral fluids of the patient.

The solid drug compositions are designed for parenteral administration, e.g., by intravenous, intramuscular, subcutaneous, intradermal, or intraparietal injection. Preferably, the compositions are administered subcutaneously.

The solid drug composition can be compounded, e.g., into an essentially non-porous cylinder, with a surface area to weight ratio of at least 10 square millimeters per milligram of the drug in the composition. This ratio can range up to 30 or more square millimeters per milligram for non-porous solid compositions, and can be up to about 100 square millimeters for porous solid drug compositions.

The drug can be, for example, insulin, luteinizing hormone-releasing hormone (LH-RH), somatostatin, or growth hormone releasing factor (GRF), and biologically active analogs thereof. The drug also can be a cytostatic compound, an analgesic compound, a hormone, or a vaccine.

The solid drug composition can be compounded with a carrier, e.g., a polymer such as a cellulose, hyaluronic acid, polyalcohol, e.g., mannitol, or sugar, or can be compounded into the solid composition without any carrier.

The invention also features a method of parenterally administering a drug to a patient, wherein the solid drug composition is injected into the patient with a device including a hollow needle that contains the solid drug composition, and a microplunger that moves within the needle and pushes the composition out of the needle into parenteral fluids of the patient.

In another embodiment, the invention features an anhydrous, solid drug composition consisting essentially of a drug, e.g., a peptide or protein, and up to 50%, or up to only 10%, by weight, of a pharmaceutically acceptable carrier, e.g., a water-soluble carrier, wherein the composition is formed into a solid cylinder having a surface area to weight ratio of at least 10 square millimeters per milligram of the drug in the composition, and wherein the drug and the carrier are selected and compounded such that when administered to a patient, the drug is dispersed from the composition upon contact with parenteral fluids and is distributed within the patient's bloodstream according to a blood level profile of the drug that is comparable to a blood level profile of the drug when administered in a liquid formulation. The composition can also include no carrier and/or be formulated into a cylinder, e.g., having a diameter of less than 0.8 mm.

The drug can be insulin, luteinizing hormone-releasing hormone (LH-RH), somatostatin, growth hormone releasing factor (GRF), or analogs thereof. The drug can also be a cytostatic compound, analgesic compound, or a hormone. The carrier in the solid composition can be a cellulose, hyaluronic acid, polyalcohol, or sugar.

The invention also features a method of making a solid drug composition including the steps of preparing a non-solid form of the drug, extruding the non-solid drug into an elongate filament, cutting the elongate filament into cylinders having a surface area to weight ratio of at least 10 square millimeters per milligram of the drug, and solidifying the cylinders to form the solid drug composition.

In particular, the non-solid form of the drug can be prepared by mixing a water-soluble carrier with a sufficient amount of a solvent to form a gel and mixing the gel with the drug to form a homogeneous, non-solid mixture, and then extruding and cutting the mixture, and solidifying the resulting cylinders by removing the solvent. In an alternative embodiment, the non-solid form of the drug is prepared by heating the drug to below a melting point of the drug, and further wherein the cylinders are solidified by cooling.

In another embodiment, the invention features an external wearable device for the automatic, controlled administration of a solid drug composition to a patient including a housing, e.g., of maximum external size of about 3.0 cm and overall thickness of 0.5 cm; a plunger located within the housing; a dispensing tube attached to the housing, the tube being designed to contain a solid drug composition consisting essentially of the drug and up to 50%, by weight, of a water-soluble pharmaceutically acceptable carrier; an actuator arranged within the housing to move the plunger from the housing into the dispensing tube; a controller that acts on the actuator to regulate the movement of the plunger through the housing and into the dispensing tube; and a power source arranged to provide energy to the actuator and the controller; wherein the plunger moves the solid drug composition out of the dispensing tube at a controlled rate.

In particular embodiments, the controller includes an electrical motor, the power source is a battery, the actuator includes two rotating wheels arranged to contact and move the plunger into the dispensing tube, and the controller includes a microcomputer or microchip programmed with a predetermined delivery profile to provide the controlled rate of delivery. In addition, the delivery tube is disposable, which allows the main part of the housing containing the controller, motor, battery, and circuitry to be reusable.

The invention also features a method of automatically administering a drug to a patient according to a predetermined delivery profile by: (a) obtaining an external wearable device as described above; (b) loading the solid drug composition into the dispensing tube; (c) inserting the dispensing tube into the patient; (d) programming the controller of the device to cause the actuator to move the plunger through the dispensing tube according to a predetermined delivery profile; (e) providing energy to the controller and the actuator to move the plunger within the dispensing tube to move the solid drug composition out of the dispensing tube and into the patient to deliver the drug to body fluids of the patient according to a predetermined delivery profile. In this method, the device can be attached to the patient.

The terms "analog" or "biologically active analog" are used herein to cover naturally occurring, recombinant, and synthetic peptides, proteins or polypeptides having physiological or therapeutic activity. In general, the term covers all derivatives of a peptide, protein, or polypeptide which exhibit a qualitatively similar agonist or antagonist effect to that of the unmodified, or naturally occurring peptide, protein, or polypeptide.

Unless defined otherwise, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

BRIEF DESCRIPTION OF THE FIGURES

FIGS. 2A to 2C are sectional views of a further embodiment of a syringe-like device.

FIG. 3 is a perspective view of an external wearable pump device for delivery of solid drug compositions separated into two main parts.

DETAILED DESCRIPTION

Figure 1A:
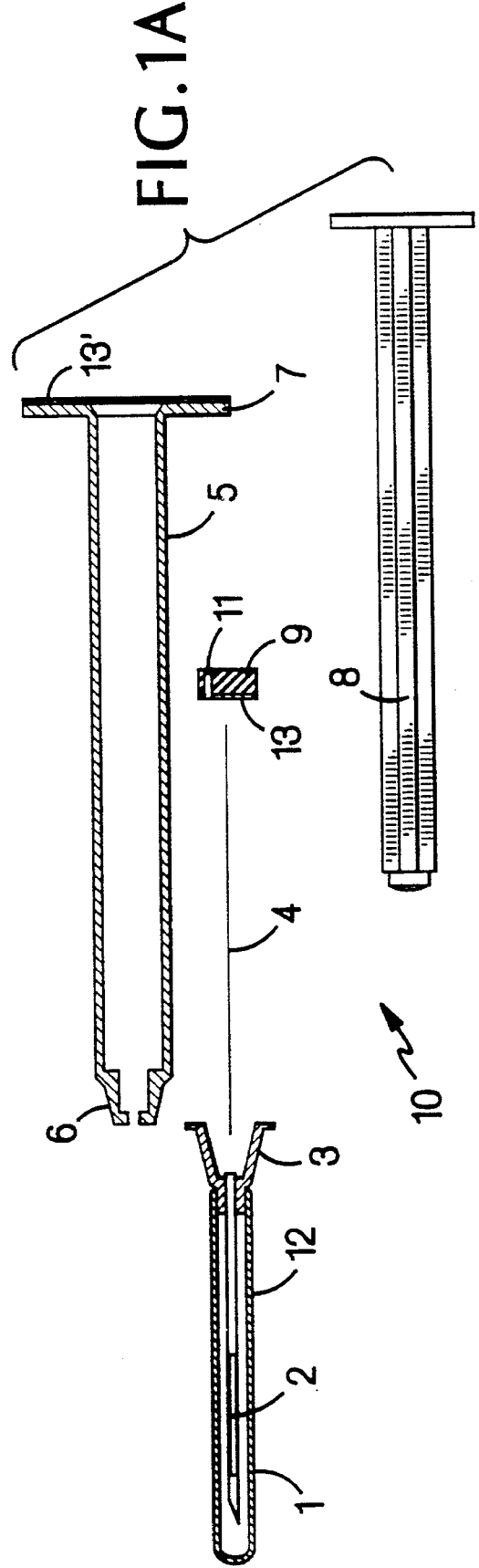
FIGS. 1A to 1C are sectional views of a syringe-like device used to inject solid drug compositions.

The invention relates to a solid drug composition delivery system including syringe-like or external pump devices specifically designed for use with new anhydrous, solid drug compositions. The syringe-like devices preferably dispense the solid drug compositions as single dosage units for immediate delivery of the drug, i.e., such that the drug is dispersed into the bodily fluids upon contact, and wherein the drug is delivered according to a blood level profile of the drug that is comparable to the blood level profile of the drug when administered in a solution formulation.

This blood level profile can be determined by taking blood samples at specific time intervals, e.g., 30 minute intervals over five hours, after the drug composition is administered, and measuring the concentration of the drug in the blood for each sample. The resulting profile is compared to a control administration of the same drug in a standard liquid formulation sampled at the same time intervals to determine whether the two profiles are comparable, e.g., whether the drug concentrations in the blood for both the liquid and solid forms are within 50% of each other at each time point after any initial peaks in concentration have stabilized.

The external pump, on the other hand, is used to administer a solid drug composition over extended periods of time, e.g., in separate dosages at predetermined time intervals, or at a constant dosage delivered slowly and continuously over one or several days. In each case, the drug is immediately dispersed into the bodily fluids from the solid composition upon injection into the body, e.g., small individual drug cylinders are delivered separately, or a long drug cylinder is slowly introduced into the bodily fluids.

Solid Drug Compositions

The solid drug compositions include one or more drugs and one or more carriers, and are preferably in the form of a miniature rod or cylinder that is rigid enough to be handled, inserted into, and injected into a patient from a delivery device. The cross-sectional shape and dimensions of these cylinders must be consistent along their length, and small enough to allow for high precision in the quantity of the drug based on a given length of the cylinder. These miniature cylinders are for example 0.1 to 5.0 cm in length and 0.1 to 0.8 mm in diameter.

The surface area to weight ratio of the solid drug compositions is also important to achieve the rapid dispersion of the drug from the composition once introduced into the bodily fluids of a patient. For a substantially non-porous solid composition, this ratio should be at least 10 $mm^2$ of surface area per milligram of the drug in the composition, and can range up to 30 $mm^2$ or more per milligram. For a porous solid composition, the surface area can be much higher, because the pores add to the total surface area. In this case, the ratio can be in the range of 100 $mm^2$ per milligram. These ratios can be achieved by preparing the solid drug cylinders as described below.

The drug or drugs are preferably distributed homogeneously throughout the solid drug composition cylinders. In addition, the drug concentration can be varied throughout the cylinder to provide a varied delivery profile in the case of extended administration with the wearable pump.

Drugs Suitable for Solid Drug Compositions

Certain drugs can themselves be formulated into a solid cylinder without any carrier. For example, so-called "pro-drugs" are polymerized from hybrid molecules of a cross-linkable drug, e.g., a drug and a cross-linkable moiety, e.g., sugar or polyamino acid, e.g., polyarginine, derivatives. Examples of drugs which do not require the presence of carriers are peptides, e.g., somatostatin analogs such as SOMATULINE® (BIM-23014), LH-RH analogs such as triptorelin, or human insulin.

In general, the composition contains at least 50% by weight of the drug and less than 50% of a carrier, and preferably less than 10% of the carrier. A typical solid drug composition will include at least 90% of the drug or drugs, depending on the physical characteristics of the carrier and the resulting rods or cylinders.

Even if a carrier is required, an advantage of the solid drug compositions is that they minimize the total amount of carrier injected into the patient. For example, in prior art liquid formulations, insulin is generally administered at 40 to 100 I.U./ml, which typically corresponds to dosages of about 2 to 4 mg/ml. Thus, the aqueous carrier comprises 99.5 to 99.8% of the total weight of the injected dosage, which is a weight ratio of 500:1 to 200:1 of carrier to insulin.

In addition, many liquid drug formulations include organic solvents or other additives, e.g., to change the pH to force the drug to dissolve in the solution. Such solvents and additives are usually toxic to the patient, even in small amounts, and thus, it is advantageous to minimize their use. Furthermore, the carriers selected for use in the present solid drug compositions are inert and have no toxic effects because the carriers need no specific properties, and are used in very low quantities.

The invention also avoids formulation and solubility problems of liquid drug solutions. Therefore, the drug compositions can include any one or more of a wide variety of drugs, even those that are insoluble or otherwise incompatible with standard liquid formulations, because the drug, e.g., in particulate form, can be merely dispersed in the carrier to form a suspension or semi-solid dispersion without dissolving the drug. The resulting homogenous mixture is then solidified, and the carrier used for the manufacturing process is eliminated. As a result, drugs that are insoluble, or that are otherwise incompatible when in solution, can be easily incorporated into a solid drug composition.

Another advantage of the invention is the increased stability of the drug in the solid composition. Drug solutions are often difficult to keep stable for prolonged periods of time. For example, drug solutions can adsorb contaminants or precipitate the active ingredient out of solution. The anhydrous, solid drug compositions largely avoid this problem. Moreover, solid compositions are not subject to the same sheer forces and turbulence that break down proteins and peptides in solution and avoid the problems of crystallization, aggregation, and coagulation associated with liquid formulations. Thus, the drug or drugs in the solid drug compositions are stable for long periods of time compared to the same drugs in a liquid formulation.

Drugs that can be used in the solid drug compositions include polypeptides such as growth hormone (GH), growth hormone releasing peptide (GHRP), growth hormone releasing factor (GRF), epidermal growth factor, interferon, insulin, somatostatin, bombesin, calcitonin, calcitonin gene related peptide (CGRP), amylin, parathyroid hormone (PTH), parathyroid hormone related peptide (PTHrp), gastrin, gastrin releasing peptide (GRP), melanocyte stimulating hormone (MSH), adrenocorticotrophic hormone (ACTH), luteinizing hormone (LH), luteinizing hormone-releasing hormone (LH-RH), cytokinases, sorbine, cholecystokinin (CCK), glucagon, glucagon-like peptide (GLP), gastrin, enkephalin, neuromedin, endothelin, substance P, neuropeptide Y (NPY), peptide YY (PYY), vasoactive intestinal peptide (VIP), pituitary adenylate cyclase activating polypeptide (PACAP), bradykinin, thyrotropin releasing hormone (TRH), taxol, or derivatives, fragments, analogs, agonists, or antagonists of any of the foregoing. This list is exemplary and not limiting.

Preferably, the drug is used for inflammation, oncology, cardiology, hormone therapy, gynecology, immunology, metabolism, or maturation. Examples of such drugs include insulin, adrenalin, xylocaine, morphine, corticoid compounds, enzymes, atropine, cytostatic compounds, analgesic compounds, estrogen, androgen, interleukin, digitoxin, biotin, testosterone, heparin, anti-platelet activating factor (anti-PAF) agents such as ginkolides (e.g., BN 52021 or BN50730, Beaufour Ipsen, France), cyclosporin, penicillin, vitamins, SOMATRIPTAN®, or diazepam. The drug can also be a therapeutic vaccine.

Carriers Suitable for Solid Drug Compositions

The carrier is chosen both to give the composition its physical characteristics and to provide an immediate delivery of the drug upon contact with bodily fluids. Furthermore, the carrier is selected not to affect the biological activity or retard the delivery of the drug, but to support and maintain the chemical stability of the drug.

The drug compositions can be manufactured using carriers which are homogeneously compounded with the solid drug or drugs. The carriers should be water-soluble and biodegradable. Suitable carriers include hyaluronic acid, gelatin, polyvinylpyrrolidone (PVP), surfactants, organic solvents, polysaccharides such as cellulose, e.g., hydroxy propyl methylcellulose (HPMC), carboxy methylcellulose (CMC), and hydroxy ethyl cellulose (HEC), sugars such as dextrose, mannose, mannitol, sorbitol, or glucose, and starches, or collagen.

Method of Preparing Solid Drug Cylinders

One method for mixing a drug and a carrier, and loading the resulting drug composition for injection via a needle of a delivery device is as follows. The carrier, e.g., hyaluronic acid, cellulose, PVP, or others listed above or known in the field, and water are added to a container, e.g., a 10 ml syringe with its end closed with a stopper. The two ingredients are mixed, e.g., using a spatula, to form a homogenous mixture, e.g., a gel. Once the gel reaches a stable structural equilibrium, e.g., after about 24 hours, it is mixed with the desired drug or drugs in another container, e.g., a 2 ml plastic syringe. The gel/drug mixture is kneaded to homogeneity, e.g., with a spatula. If the final solid composition does not include a carrier, then the drug is kneaded solely with water or another carrier, which is later evaporated.

The mixture is then transferred to an extrusion chamber, e.g., a stainless steel syringe, with an extrusion nozzle, e.g., a needle with a 0.3 to 0.8 mm internal diameter attached to the syringe. The gel/drug mixture (or water/drug mixture) is extruded and cut into cylinders of a precise length for administration, and collected, e.g., on a glass slide. The resulting cylinders are thoroughly dried in a vacuum, e.g., for 24 hours at room temperature. Alternatively, the cylinders can be extruded into longer rods, dried, and then cut into shorter cylinders of the precise length required for administration.

Other standard techniques, such as fusion extrusion or wet or dry spinning, can be used to create the solid drug cylinders. All of these techniques involve moving a non-solid mass of material through an orifice with a particular shape that produces an elongated cylinder or rod with a desired cross-section. This cylinder or rod can be directly dried or otherwise solidified, or can be stretched and then solidified. The material is made non-solid by heating or adding a solvent, and is returned to a solid state by cooling or removing the solvent, e.g., by evaporation, freeze drying, or vacuum drying, respectively.

The cylinders are then tested to determine the precise mass percentage of drug, i.e., dosage per length of cylinder. Five cylinders are taken from a batch, weighed, and then the total amount of drug is removed from each cylinder, e.g., by solubilization in an appropriate solvent such as acetic acid 0.1% in water, and is measured using standard HPLC methodology. For example, when the drug is insulin, a chromatograph column of Kromasil-C8 5 µm 25×0.46 cm can be used. The mobile phase is an isocratic mixture of acetonitrile and 0.1% triethylamine in 0.2M $Na_2SO_4$, pH of 2.3. The various drug components are detected under UV at 220 nm. The solvent for the sample is 0.05N HCl and 0.2 mM cetyl-trimethyl-ammonium bromide (Sigma).

Prior to use, the cylinders are also tested for uniformity by calculating their weight/length ratio. Ten cylinders are weighed and their length is measured and averaged. A cylinder is acceptable only if the Relative Standard Deviation (RSD) is less than 1%. This RSD equals the (standard deviation of the length/weight ratio÷mean)×100, so it is a measure of the uniformity of the weight/length ratio.

As a quality control measure, batches of the cylinders can be tested for friability, i.e., the propensity of the cylinders to crumble or break into smaller pieces when subjected to disruptive forces. This can be determined by placing a specific amount, e.g., 1 to 10 mg, of cylinders that are known to be of equal size into a 5 ml TEFLON® grinding cup of a ball mill (MIXER MILL type MM-2, RETSCH, West Germany) with one steel or agate ball, e.g., of 7 mm diameter. The cup is shaken horizontally at, e.g., 20% of the full power of the machine for five minutes. The resulting material is then sieved using a screen of predetermined mesh size (400 microns). The percentage of material passing through the screen is then taken as a measure of cylinders' friability or strength and the acceptable friability is determined as a function of the delivery device to be used, the length and diameter of the solid drug cylinders, and the injection route.

Once the cylinders have been accepted, the dosage is determined by length and weight measurement. The cylinders are cut into precise lengths corresponding to desired dosage units. The cylinders are tested once more prior to administration by weighing them on a microbalance (Mettler UMT 2). The cylinders are then ready to be loaded into hollow needles.

Pre-loading of hollow needles is accomplished through the back end of the needle. The tip is first sealed with an inert biomaterial layer such as gelatin or hyaluronic acid. The back end of the needle preferably has a funnel shape which makes it easy to insert the solid drug cylinder and a microplunger used to push the cylinder out of the tip of the needle and into a patient.

In a preferred embodiment, the back end of the needle is attached to a sterile plastic or glass cylinder into which the solid drug cylinder is extruded and dried. When dried, the cylinder simply falls into the needle due to gravity. The pre-loaded needle is then ready to be attached to a syringe-like or an external pump delivery device as described below. This sterile plastic or glass cylinder also helps prevent the device from inadvertently dispensing the solid drug composition.

A Syringe-Like Delivery Device

A syringe-like delivery device for the solid drug cylinders that includes a hollow syringe barrel, a needle, and a microplunger and piston assembly, is easily made using existing technologies. The needle can be a standard hollow needle, e.g., a hypodermic needle. The microplunger, which pushes the drug cylinder out of the needle and into the patient, can be a stainless steel shaft as used in chromatography syringes, e.g., Hamilton syringes. The piston or guide that pushes on the microplunger is an inexpensive and simple plastic accessory, which can be smaller and lighter than a 1 ml syringe, and can be reused with many different pre-loaded needles.

Figure 1B:
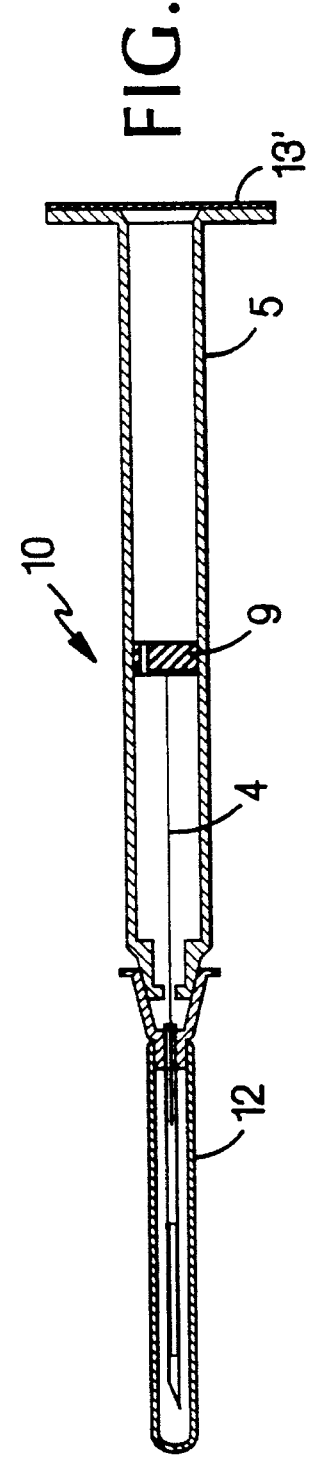
Figure 1C:
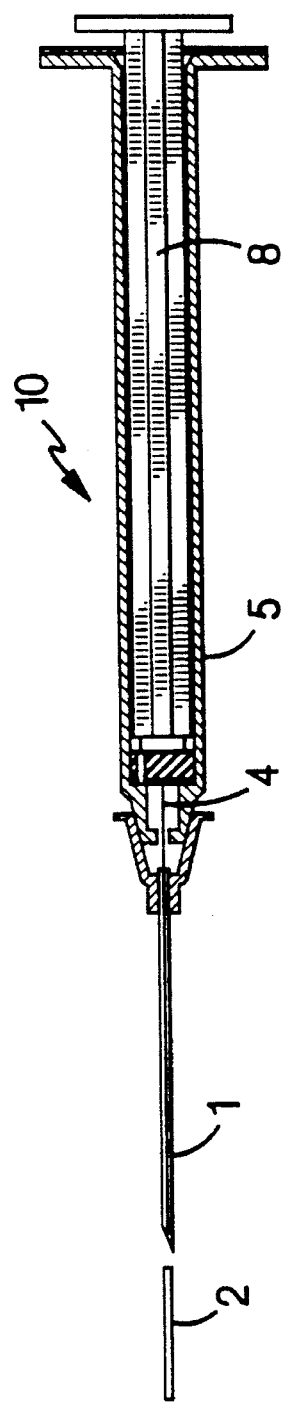

FIGS. 1A to 1C show an injection device 10 that comprises a hollow needle 1 pre-loaded with a single dose of a solid drug composition 2, e.g., in the form of a cylinder, to be injected. The diameter of the needle is variable, e.g., 0.45 mm, 0.6 mm, or 0.8 mm, and any diameter between 0 and 2 mm is suitable. Needle 1 is fitted with a sleeve 3, which allows the needle to be connected to a nozzle 6 at the end of syringe barrel 5.

Microplunger 4 is engaged in the hollow channel in needle 1 in contact with the drug 2. The microplunger can be made of, e.g., stainless steel or plastic. Because the drug composition is a solid, a waterproof seal is not needed around microplunger 4, and in fact the microplunger preferably has a diameter 0.01 or 0.02 mm less than the inside diameter of the needle. For example with a 0.45 mm needle, the inside diameter of the needle is 0.27 mm, and the preferred diameter of the microplunger is 0.25 mm. Furthermore, the microplunger is preferably not airtight so that the drug cylinder is injected into the body fluids without also injecting a significant amount of air into the body fluids at the same time.

Barrel 5 has at its proximal end two small flanges 7. A plunger stick 8 is movable within barrel 5 to push microplunger 4 into needle 1 and to expel drug cylinder 2. The device further comprises a rubber plunger 9, which has a protective film 13, e.g., of aluminum or paper, on the side which, in use, abuts microplunger 4, and an air passage 11. During assembly of the device, air between the end of microplunger 4 and drug cylinder 2 is expelled from the space between microplunger 4 and needle 1. As shown in FIG. 1B, during storage, loaded needle 1 is protected by a cap 12, and barrel 5 is sealed by a protective film 13', e.g., of aluminum or paper, that seals the barrel at flanges 7.

As shown in FIG. 1C, drug cylinder 2 is dispensed from needle 1 by inserting plunger stick 8 into barrel 5, either by removing or piercing film 13', and then pushing on plunger stick 8 to contact plunger 9 and push microplunger 4 further into needle 1, causing drug cylinder 2 to be expelled from the end of needle 1. The lengths of the plunger stick and the microplunger are selected so that when the microplunger is at its maximum depth in the needle, the microplunger does not extend beyond the tip of the needle, or does not extend by more than a few millimeters.

The same microsyringe can be loaded with different quantities of drugs by simply adjusting the microplunger 4 and plunger 9 into different positions or with different lengths. In preferred embodiments, the composition is pre-loaded into the needle.

FIGS. 2A to 2C show another injection device 20 that includes a hollow needle 1 pre-loaded with a single dose of a solid drug cylinder 2 to be injected. The tip of needle 1 can be sealed with a protecting film 1', e.g., by dipping the needle into a gel of HPMC 2%, or the entire needle can be covered with a cap as shown in FIG. 1B. The other end of needle 1 is of conical form and is set into a guide member 23. Microplunger 4 has one end engaged in the hollow channel in needle 1 in contact with the drug cylinder, and its other end fitted with a head 25. Guide member 23 is provided with a grip portion 26 to be gripped by the user. Two extensions 27 carried by grip portion 26 are shaped so as to receive and hold head 25 of microplunger 4 and prevent its accidental movement, thereby safeguarding against premature expulsion of the drug cylinder before insertion of the needle into the patient. A slight inward pressure on extensions 27 allows head 25 to move over them and along guide member 23, pushing microplunger 4 into the hollow channel of needle 1 to expel the drug cylinder.

External Wearable Pump

FIGS. 3 to 7 show various embodiments of external wearable pumps to deliver solid drug compositions over extended periods of time, e.g., several days to weeks.

FIG. 3 shows an external wearable pump 30 separated into a permanent housing portion 32 and a disposable housing portion 34, which can each be machined or molded from a suitable heat resistant, chemically inert, rigid material, e.g., polyvinylchloride, polycarbonate, TEFLON®, POLYSULFONE® (AMOCO), or stainless steel. A central plunger 36 passes through the device and delivers the drug composition loaded into needle 38 into the patient in a precisely controlled manner. Needle 38 is connected to a dispensing tube 40, e.g., of metal, that can include guide tab 42, which is used to insert the needle into the patient. Guide tab 42 is preferably made of a flexible plastic or rubber and is either attached to or molded as a part of dispensing tube 40. Dispensing tube 40 is attached to exit guide tube 50 via connector 51.

Both housing portions can be transparent to facilitate the determination of whether plunger 36 is properly moving through the device. The external dimensions of the housing are preferably about 3 cm or less in diameter and 0.5 cm in height. Permanent portion 32 and disposable portion 34 are preferably attached together by frictional force.

Figure 4:
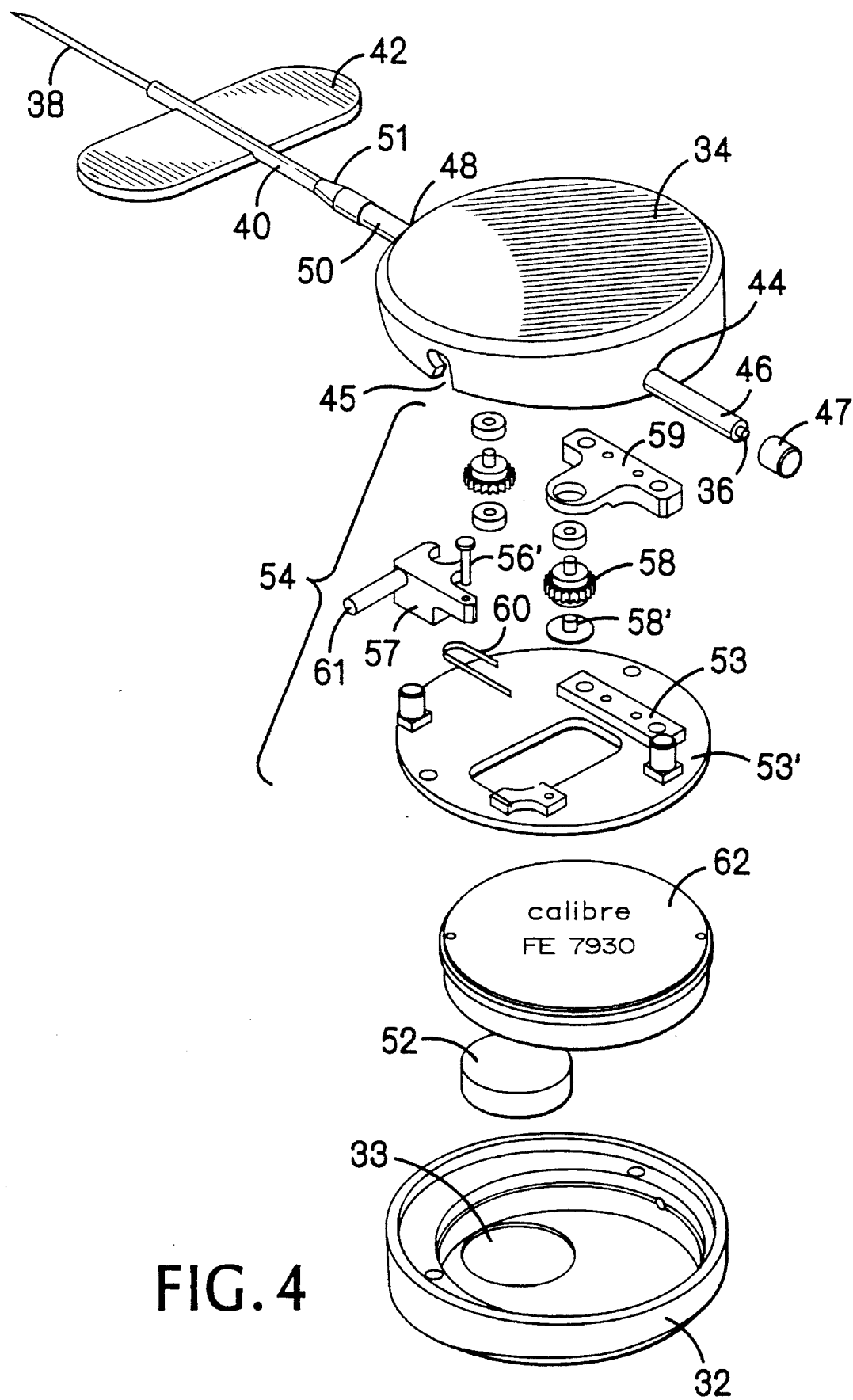
FIG. 4 is an exploded view of the device of FIG. 3.
Figure 5:
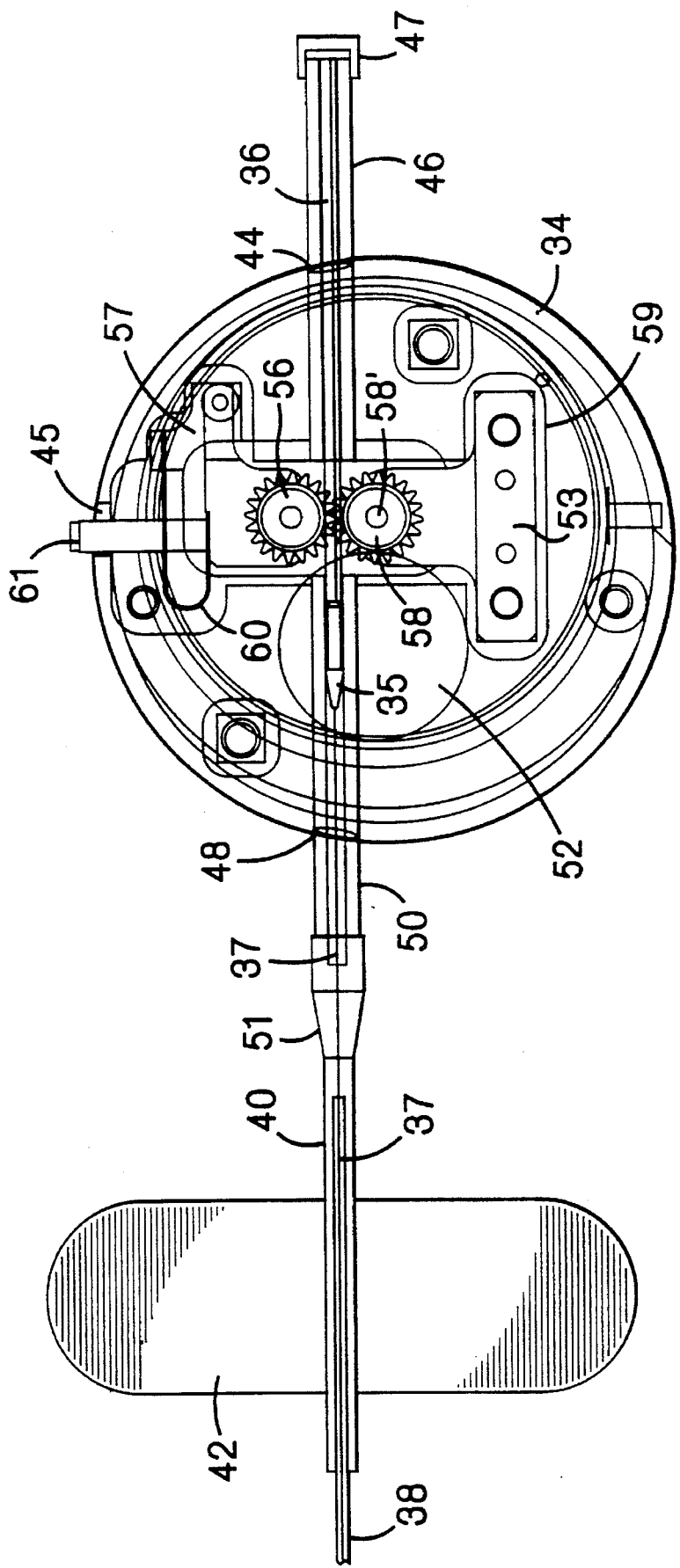
FIG. 5 is a top cross-sectional view of the device of FIG. 3.
Figure 6:
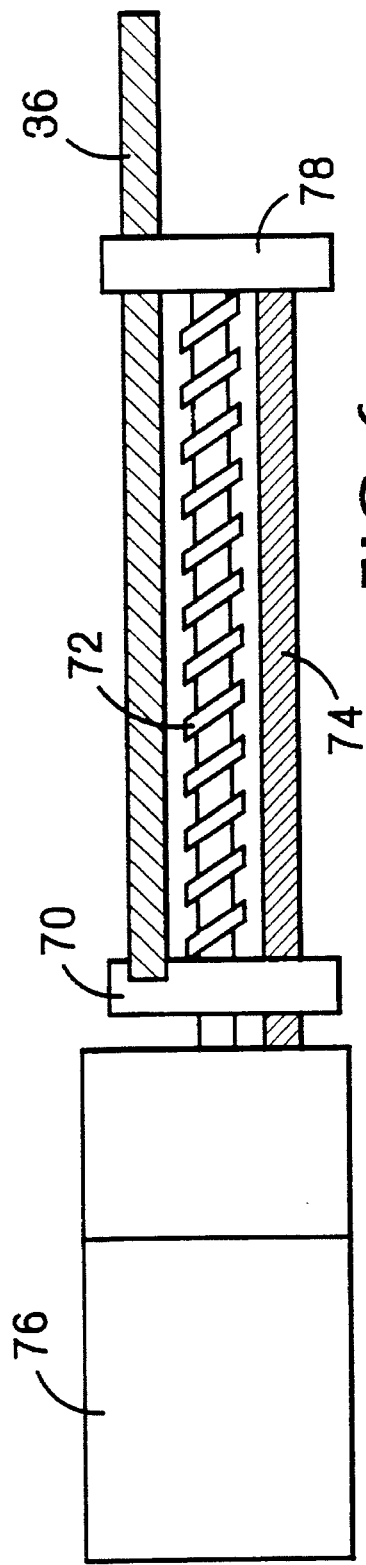
FIG. 6 is a schematic side view in partial cross-section of another embodiment of the external wearable pump for delivery of solid drug compositions.

With reference to FIGS. 4 and 5, disposable housing portion 34 has three openings. Opening 44 allows the attachment of plunger guide tube 46, while opening 48 allows the attachment of plunger exit guide tube 50. These two hollow tubes 46 and 50 allow plunger 36 to pass through the disposable portion 34, and provide protection and guidance for the plunger. Cap 47 attaches to guide tube 46 to restrict the movement of plunger 36 into the device. Opening 45 is part of a clip system to connect the permanent portion 32 of the housing to the disposable portion 34 by moving wheel 56 (and axle 56' and wheel holder 57) aside with lever 61 against the force of spring 60 to allow plunger 36 to nest between wheels 56 and 58.

The external surface of disposable housing portion 34 can be coated with an adhesive to attach device 30 to the skin of a patient. Such adhesives need not be too strong, because the device is very light, and should secure the device but be easily removable without severe discomfort to the patient.

Permanent housing portion 32 has one opening 33 which allows easy removal of battery 52 without disturbing other parts within the housing. Permanent housing portion 32 encloses an actuator assembly 54 which moves plunger 36 through exit guide tube 50. Actuator 54 includes two wheels 56 and 58. These wheels are attached to the actuator by wheel holders 57 and 59, respectively. Wheel holder 59 is secured to support 53, which is secured to base plate 53' of actuator assembly 54.

The wheels rotate in opposite directions such that plunger 36 is moved between them and through the housing, converting rotational into translational motion. Preferably, the spacing between the two wheels is slightly less than the diameter of the plunger. The wheels are preferably manufactured from stainless steel or plastic. These wheels can be toothed gear wheels or smooth-surfaced wheels or rollers, e.g., of rubber or plastic, without gear teeth, as long as they can contact and move the plunger through the exit guide tube 50. The pressure that the wheels exert on the plunger is regulated by spring 60 which forces the two wheels towards each other. Wheel 56 is attached to wheel holder 57 by axle 56'. Wheel 58 is attached to both wheel holder 59 and electrical motor 62 by axle 58'.

Plunger 36 is preferably manufactured from a suitable rigid material, e.g., stainless steel or plastic, and includes a tip 35 that contacts microplunger 37, also of stainless steel, which moves within needle 38. The plunger can be smooth surfaced or have ridges or teeth to interact with gear wheels 56 and 58. Preferably, microplunger 37 is of a diameter slightly less than the internal diameter of needle 38 (e.g., 0.3 to 0.8 mm) and of a length longer than the length of needle 38 (e.g., 3 cm). Preferably, plunger 36 is disposable. New plungers can be loaded into plunger guide tube 46, through wheels 56, 58, and into exit guide tube 50.

The power supply for the device in this embodiment is an electrical motor 62 powered by battery 52, e.g., a 1.5 V battery. The motor rotates axle 58' which engages wheel 58, which in turn causes the second wheel 56 to rotate in the opposite direction. The motor can be an inexpensive one-step watch motor or movement, which is usually less than 2 cm by 3 mm. In the case of the watch motor, the power can be transmitted to the actuator wheels by either the hour or minute hand axle.

Suitable watch movements include F.E. 7930, 6220, and 6230 (France-Ebauches, S.A.)(size 6¾ mm or 8 mm), Ronda Harvey 375 1.5 V motor (10% mm), Ronda 313 (11% mm), and ISA 1198 (11½% mm). Other possible motors include continuous current motors, e.g., Maxon DC motor (2.8 to 12 mm diameter) or Arsape AM 15-24 or AM 10-20 motor, or stepper motors, e.g., Arsape single phase stepper motors P130-S130 or P141, or MMT two phase stepper motors. Other types of motors can be used, e.g., a spring-powered shape memory alloy-powered mechanical motor, an electromagnetic motor, or an osmotically or electrochemically driven motor, as long as the power can be converted into a force that moves the plunger through the housing.

When utilizing a watch motor, the translational speed of the plunger is determined by the diameter of wheel 58 and its position on either the hour or minute axle of the motor. The speed of the wheel can also be controlled by adding another wheel of a different radius between axle 58' and wheel 58. When not utilizing a watch motor, one can add a separate transmission to modulate the translational speed of the plunger.

The motor can include a control mechanism such as an integrated circuit or microprocessor and related circuitry which controls the motor and is pre-programmed to a desired delivery profile. Such microchips and microprocessors and related circuitry are known in the art and can be easily adapted to control an electric motor for use in the present devices. Examples of such electrical control mechanisms are described, e.g., in U.S. Pat. Nos. 5,049,141 and 4,265,241. The power supply for this circuitry could be battery 52, or an additional, separate battery.

Plunger exit guide tube 50 is attached to dispensing tube 40 by connector 51, which is preferably molded directly to dispensing tube 40. Connector 51 is preferably manufactured from silicon or TYGON®. The external diameter of exit guide tube 50 is approximately the same as the internal diameter of connector 51, thus allowing a strong frictional seal when connector 51 is attached to exit guide tube 50. Dispensing tube 40 is preferably one part of the hollow metallic tube of needle 38, or needle 38 can be a separate part inserted into dispensing tube 40. The needle is preferably a subcutaneous or butterfly needle.

Dispensing tube 40 and needle 38 are loaded with a solid drug composition. In preferred embodiments, the needle and tube are pre-loaded with the solid drug composition, e.g., as described above or by other standard loading techniques, and the composition is located between the tip of the needle and the connector 51. The internal diameter of the needle (e.g., 0.27 mm) should be slightly larger than the external diameter of both the drug composition (e.g., 0.25 mm) and microplunger 37 (e.g., 0.25 mm) that pushes the drug through tube 40 and into needle 38.

The inside of dispensing tube 40, and, if desired, the entire housing, can be filled with a biocompatible oil to insure that the tube and the housing remain watertight. Suitable oils include silicon oil, Dow Corning 344 medical fluid, Miglyol 812 Dynamit oil, castor oil, isopropyl myristate, ethyl oleate, or injectable olive oil. The oil prevents aqueous liquids, e.g., bodily fluids or water, from entering the housing through the dispensing tube or needle, e.g., when the patient is bathing or showering.

In other embodiments, the actuator is a mechanism in which a motor rotates a screw. With reference to the schematic of FIG. 6, plunger 36 is attached to a nut 70, which moves along screw 72 and rod 74 as screw 72 is rotated by motor 76. Plunger 36 is stabilized by plunger guide 78, connected to rod 74.

Figure 7:
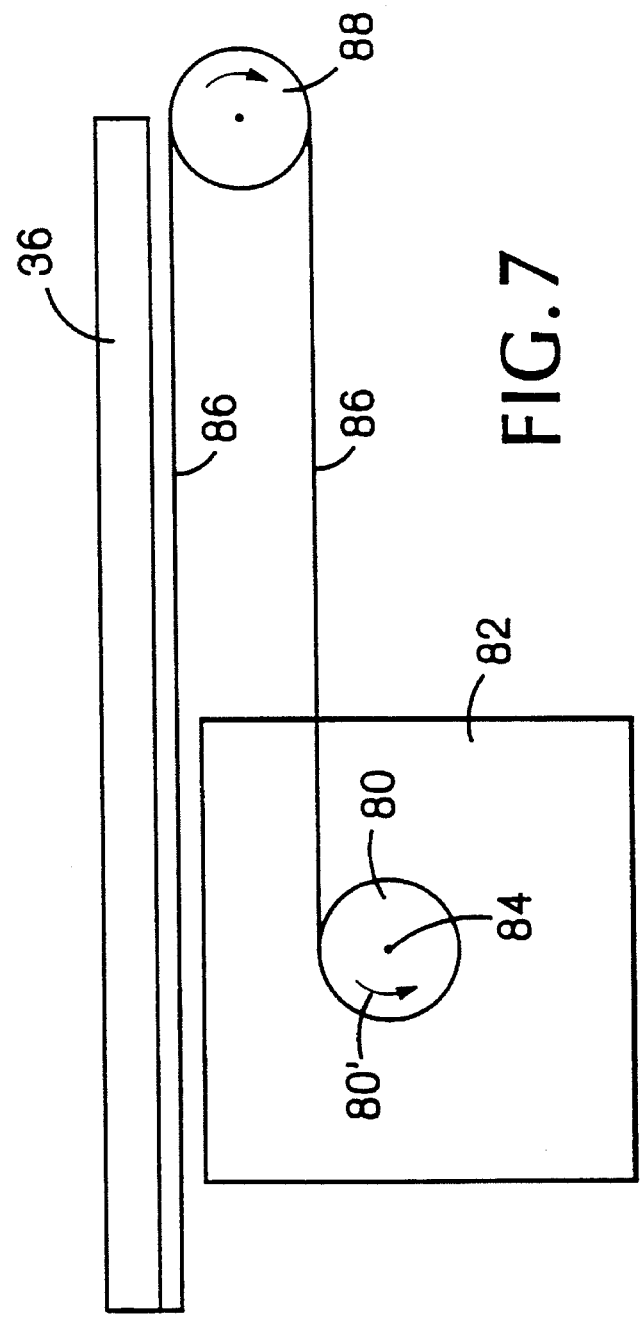
FIG. 7 is a schematic side view of another embodiment of the external wearable pump for delivery of solid drug compositions.

The schematic of FIG. 7 shows an embodiment in which the actuator is a pulley mechanism. In this embodiment, bobbin 80 is attached to motor 82 by axle 84. A filament or wire 86 is connected to bobbin 80, passes around pulley 88, and is connected to plunger 66. As bobbin 80 is rotated by motor 82 in the direction of arrow 80', plunger 36 is pulled towards pulley 88, and causes a drug composition to be pushed out of a needle (not shown).

EXAMPLES OF SOLID DRUG COMPOSITIONS

EXAMPLE 1

100% Human Insulin 81.52 mg of water was added to 81.86 mg of insulin. The mixture was kneaded with a spatula in a 1 ml plastic syringe and subsequently added to a stainless steel syringe, which had an internal diameter of 2.3 mm and a needle with an internal diameter of 0.3 mm. The mixture was extruded through the syringe using a Harvard syringe pump. The resulting extruded rods were cut into cylinders at a length of 1.5 cm and collected on glass slides. The cylinders were then allowed to dry under vacuum for 24 hr. The resulting cylinders contained 0.470 mg (12.69 I.U.) of insulin/cm (19.035 I.U. total). The cylinders were loaded into needles of 0.5 mm internal diameter and 15 mm in length.

Recombinant human insulin (RHI) is pure, water soluble insulin, while bovine pancreas insulin (BPI) is zinc insulin, which is water insoluble, and is usually prepared in 16% glycerol. RHI and BPI each provide about 26 to 28 Insulin Units (IU) per mg depending on the purity of the insulin. Therefore a 10 IU solid drug cylinder can be made to contain 0.5 mg, and be 1.0 cm long, and 0.3 mm in diameter. A 20 IU cylinder would contain 1 mg, and be 2 cm×0.3 mm. A 40 IU cylinder would contain 2 mg, and be 4 cm×0.3 mm.

Figure 8:
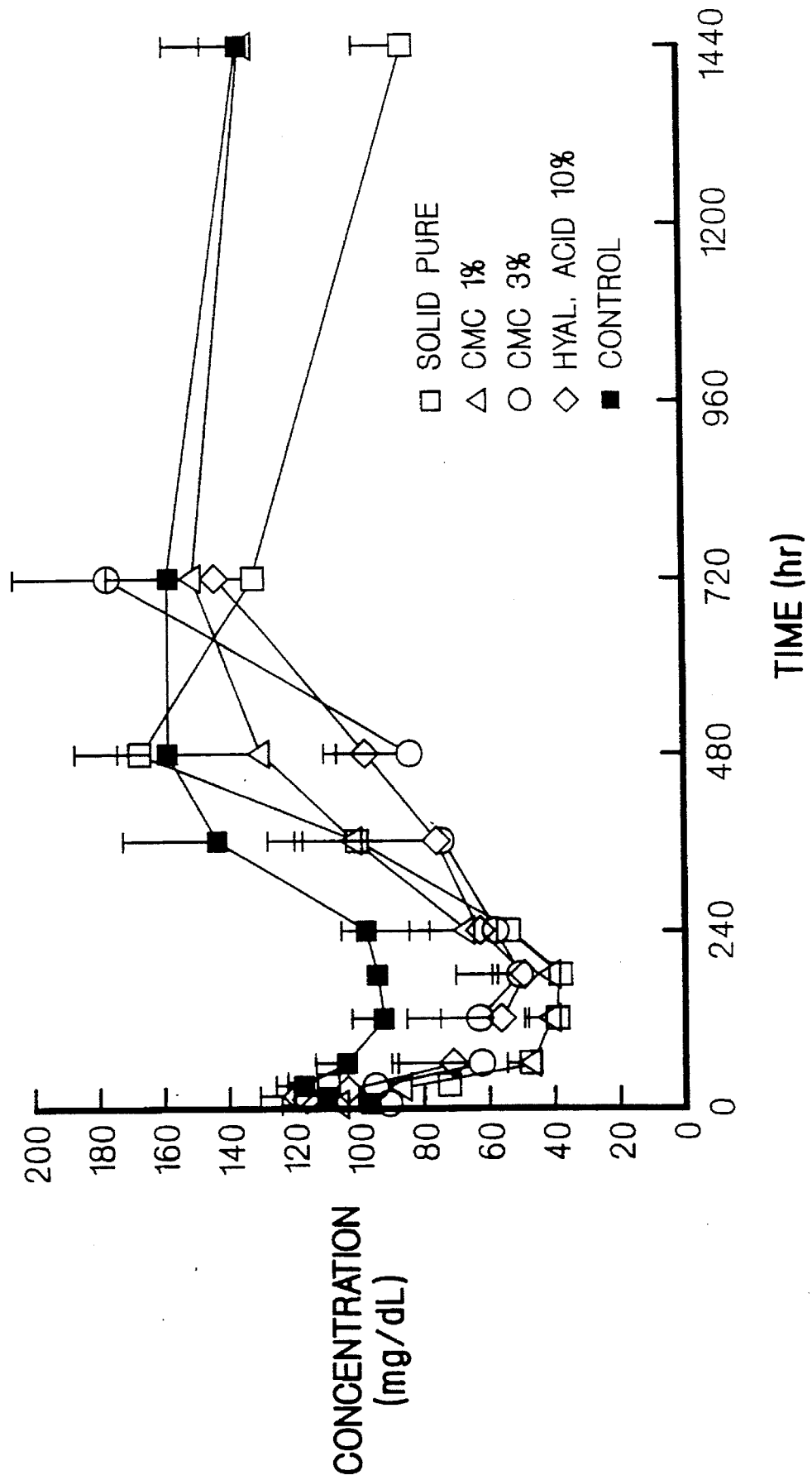
FIG. 8 is a graph comparing plasma glucose levels in rats injected with bovine insulin in different solid formulations versus a standard liquid formulation.

Different doses of solid insulin can be compared with a standard liquid injectable formulation that contains the same quantity of IUs in 0.5 ml of physiological serum or in a 16% glycerol formulation. FIG. 8 shows the hypoglycemic effect of insulin drug cylinders and controls of liquid formulations of the same dosage (0.6 IU) of insulin (BPI) in vivo in non-diabetic Sprague-Dawley rats. The solid drug cylinders (e.g., □) were just as effective as the liquid insulin formulation control (■) in terms of intensity and rapidity of action on the glucose plasma levels in the rats. This confirms the possibility of using the solid drug compositions instead of the standard liquid formulations.

For insulin therapy, using a solid drug delivery device provides a clear advantage; patients have to carry only small caps or blister-packs of micro-syringe needles pre-loaded with different dosages of insulin (e.g., 10 IU, 20 IU, or 40 IU) and the small reusable delivery device. Without any preparation, the patient connects the pre-loaded needle of his choice to the device and can self-administer the proper dosage of insulin in a relatively painless fashion. The solid drug composition is stable for a longer time at room temperature than any liquid formulation.

EXAMPLE 2

90% Human Insulin, 10% Hyaluronic Acid 0.75 g of sodium hyaluronate and 9.25 g of water were mixed to form a gel. 0.11496 g of the resulting gel was mixed with 0.07761 g of insulin. The mixture was kneaded and extruded. The resulting extruded rods were cut at a length of 1.5 cm and collected on glass slides. The resulting 1.5 cm cylinders were then allowed to dry under vacuum for 24 hr., and contained 0.514 mg (13.87 IU) of insulin/cm (weight percentage 10% hyaluronic acid and 90% insulin). Therefore, each cylinder contained 1.5 cm×13.87 IU/cm= 20.8 IU.

Figure 9:
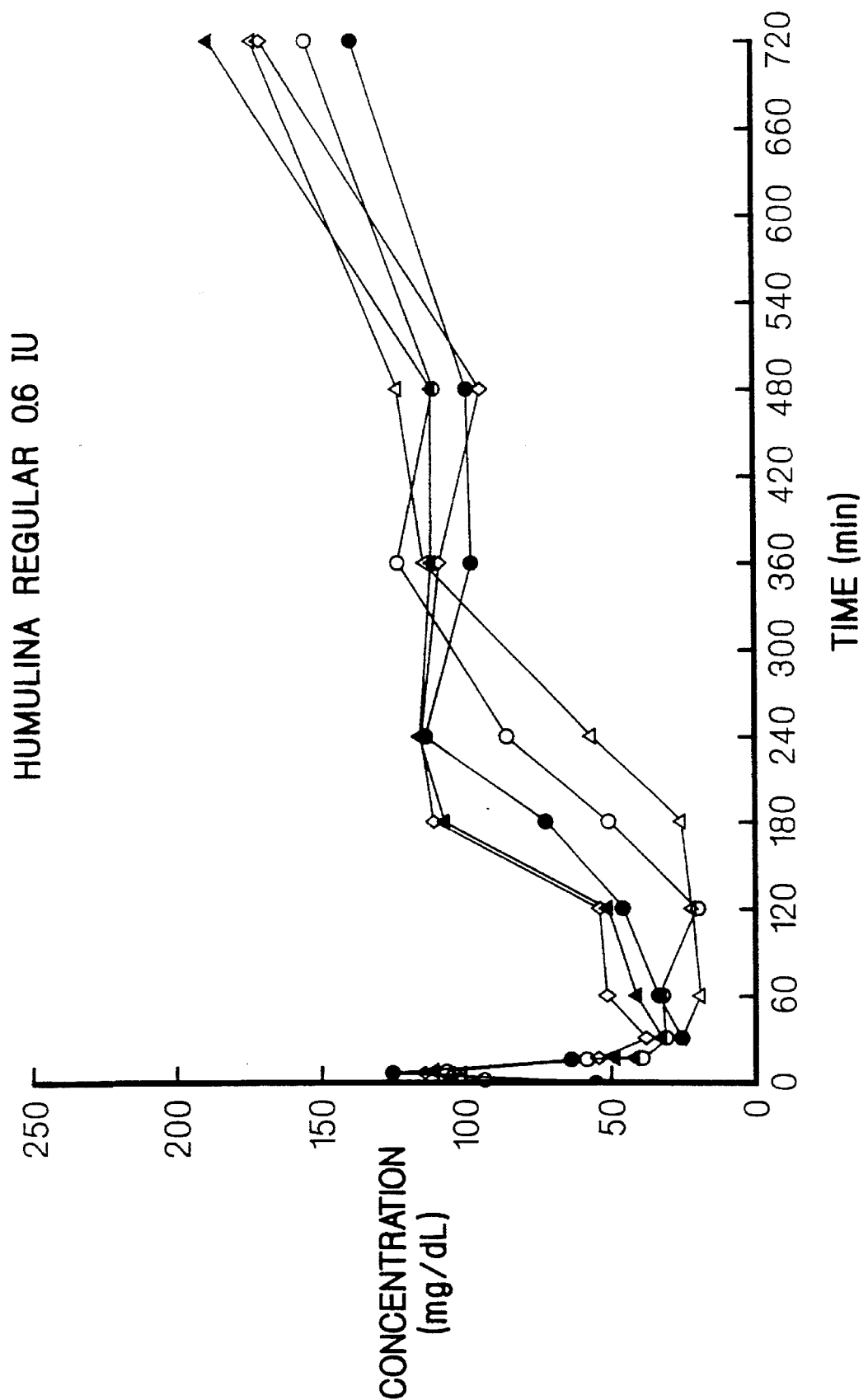
FIG. 9 is a graph of plasma glucose levels in rats injected with a standard liquid insulin solution.
Figure 10:
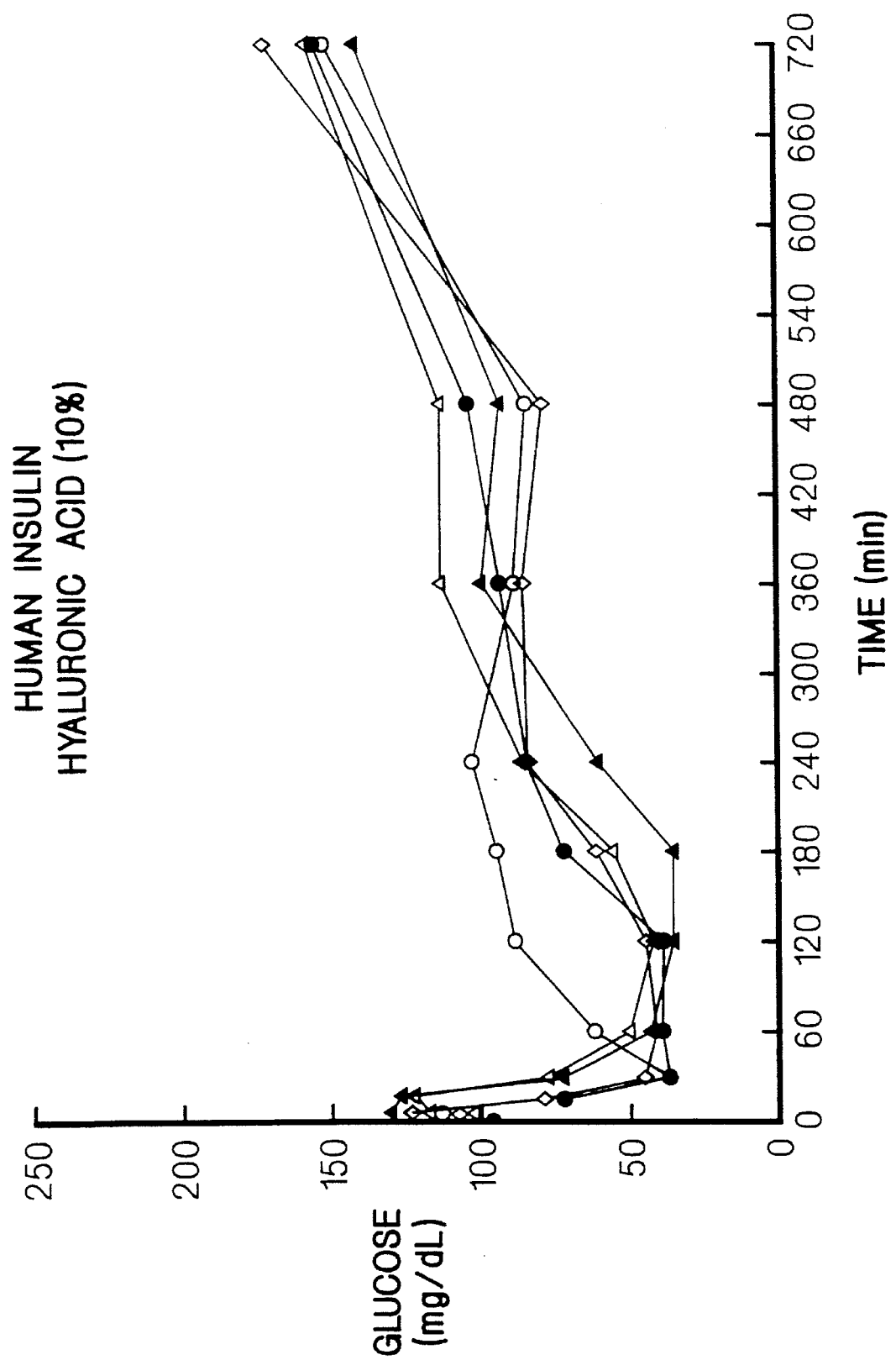
FIG. 10 is a graph of plasma glucose levels in rats injected with a solid composition containing 90% human insulin and 10% hyaluronic acid.
Figure 11:
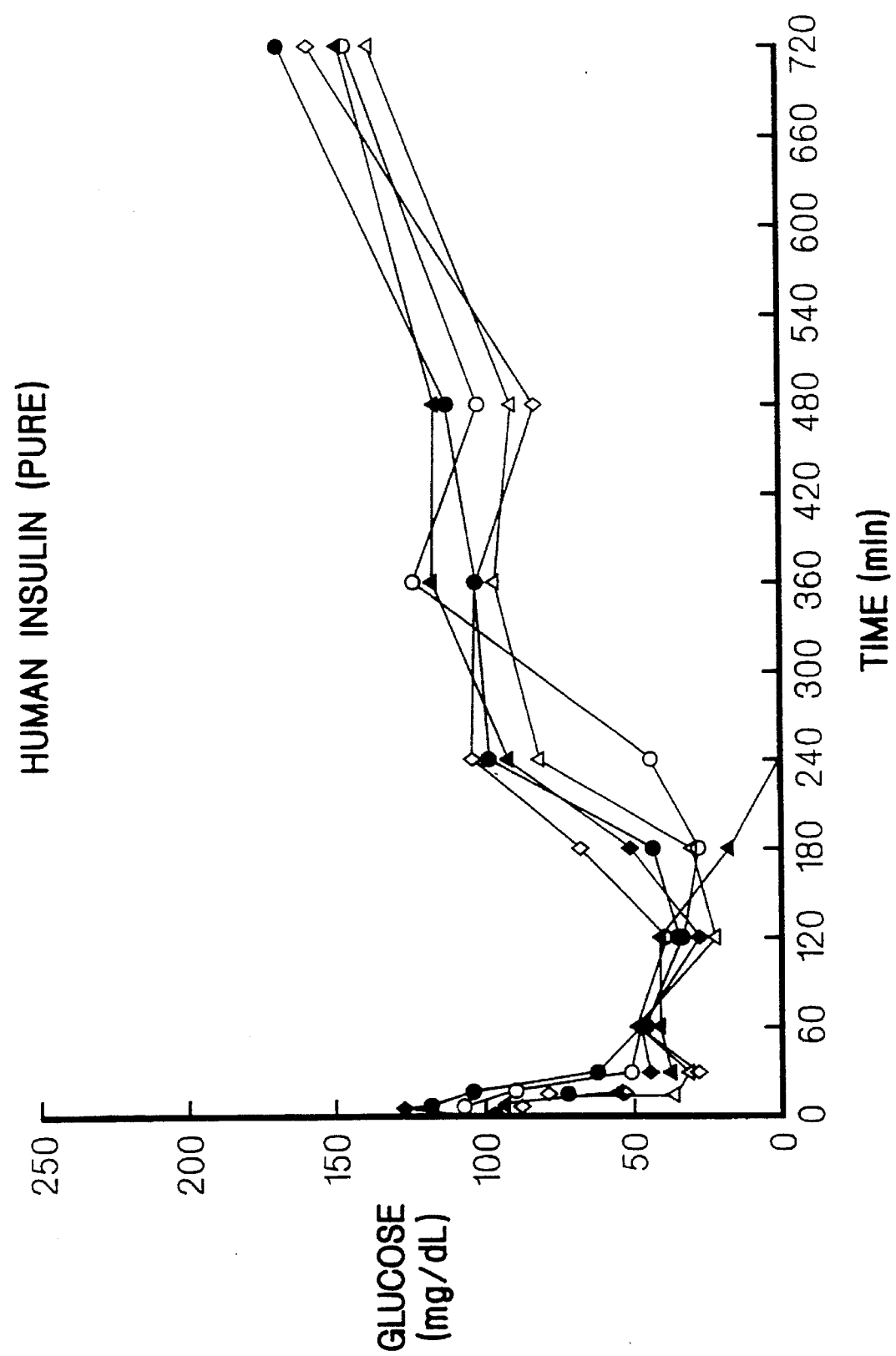
FIG. 11 is a graph of plasma glucose levels in rats injected with a solid composition containing 100% pure human insulin.

Experiments in rats (n=5) injected with various formulations of insulin (0.6 IU) confirm that the effect on the plasma glucose level of a commercial insulin solution (Humulina regular) (FIG. 9) is substantially the same as that of a 90% insulin/10% hyaluronic acid solid composition (FIG. 10) and 100% insulin in solid form (FIG. 11).

EXAMPLE 3

90% Bovine insulin, 10% Hyaluronic Acid

The above protocol was performed by mixing 0.75 g of Na hyaluronic acid and 9.25 g of water. 0.30936 g of the resulting gel was added to 0.20848 g of bovine insulin. The mixture was extruded and cut. The resulting 1.5 cm cylinders contained a total a dosage of 22.17 IU of insulin (weight percentage 10% hyaluronic acid/90% bovine insulin).

FIG. 8 shows the plasma glucose level in rats injected with a solid drug composition including 90% bovine insulin and 10% hyaluronic acid (◊) at a dosage of 0.6 IU per rat. The effect on the plasma glucose level is substantially the same as that of the insulin solution control (■) and the 100% insulin solid formulation (□).

EXAMPLE 4

97% Bovine Insulin, 3% Carboxy Methylcellulose

The above protocol was performed by mixing 0.3 g of carboxy methylcellulose (CMC) and 9.7 g of water. 0.15964 g of the resulting gel was added to 0.14129 g of bovine insulin. The mixture was extruded and cut. The resulting 1.5 cm cylinders had a total dosage of 26.58 of insulin (weight percentage 3% CMC and 97% bovine insulin).

The effect of this solid bovine zinc insulin formulation (o) was compared to other formulations of bovine insulin (FIG. 8). The results show that the 97% BPI/3% CMC formulation provided substantially the same hypoglycemic effect and duration of action as the liquid insulin solution control (■) and the 100% insulin solid formulation (□).

EXAMPLE 5

100% SOMATULINE® (BIM-23014C)

The above protocol was performed by mixing 175.43 mg of water and 75.43 mg of the acetate salt of a somatostatin analog, SOMATULINE® (BIM-23014C, Biomeasure, Milford Mass.). The mixture was extruded through a 2.3 mm syringe (0.5 mm internal diameter needle) and cut. The resulting 3.6 cm cylinders had a dosage of 0.624 mg/cm. The cylinders were loaded into needles of 0.8 mm external diameter.

Figure 12A:
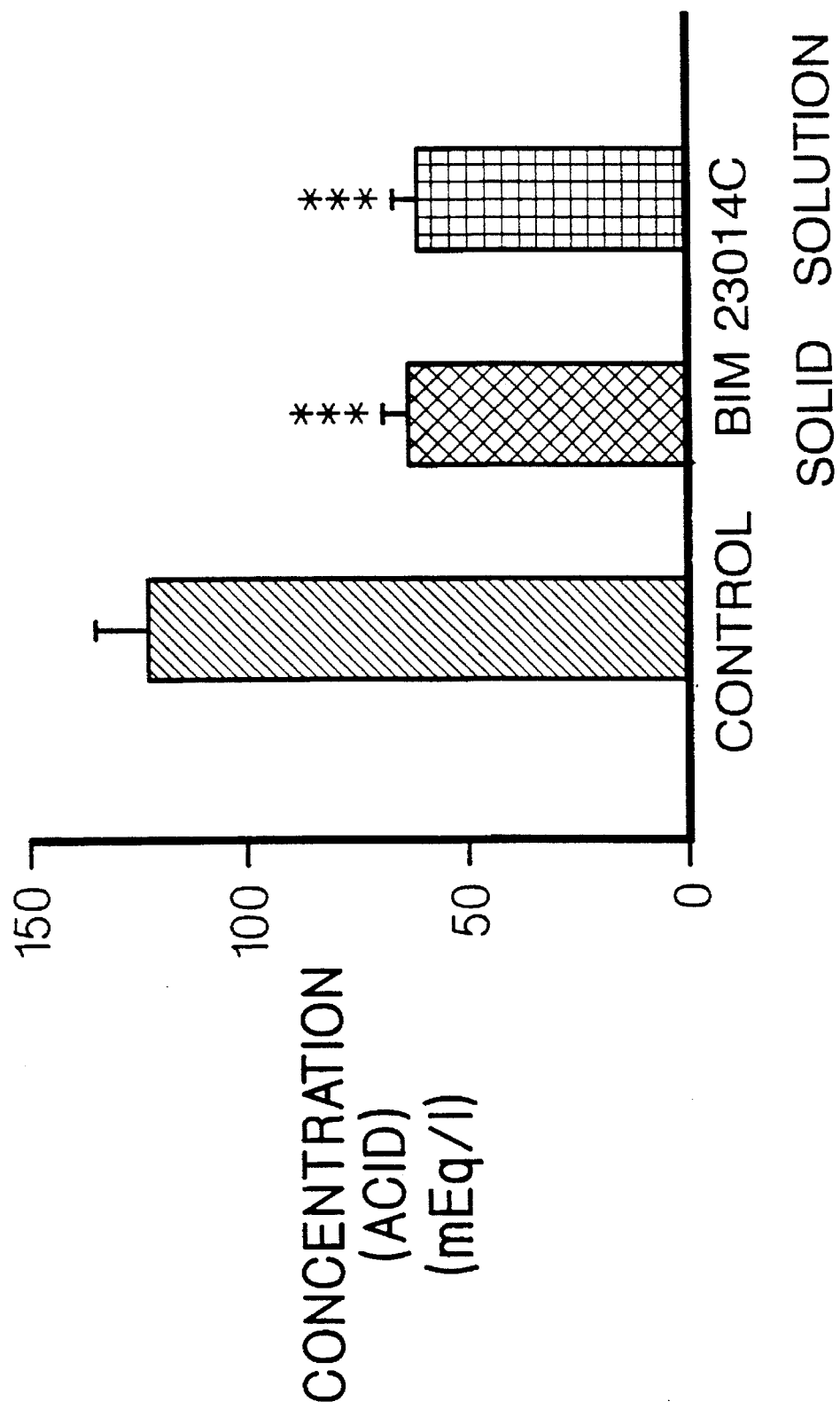
FIGS. 12A to 12C are bar graphs showing the effects of a solid composition of a somatostatin analog (BIM 23014C), a standard liquid solution of BIM 23014C, and a control, on gastric hypersecretion in rats.
Figure 12B:
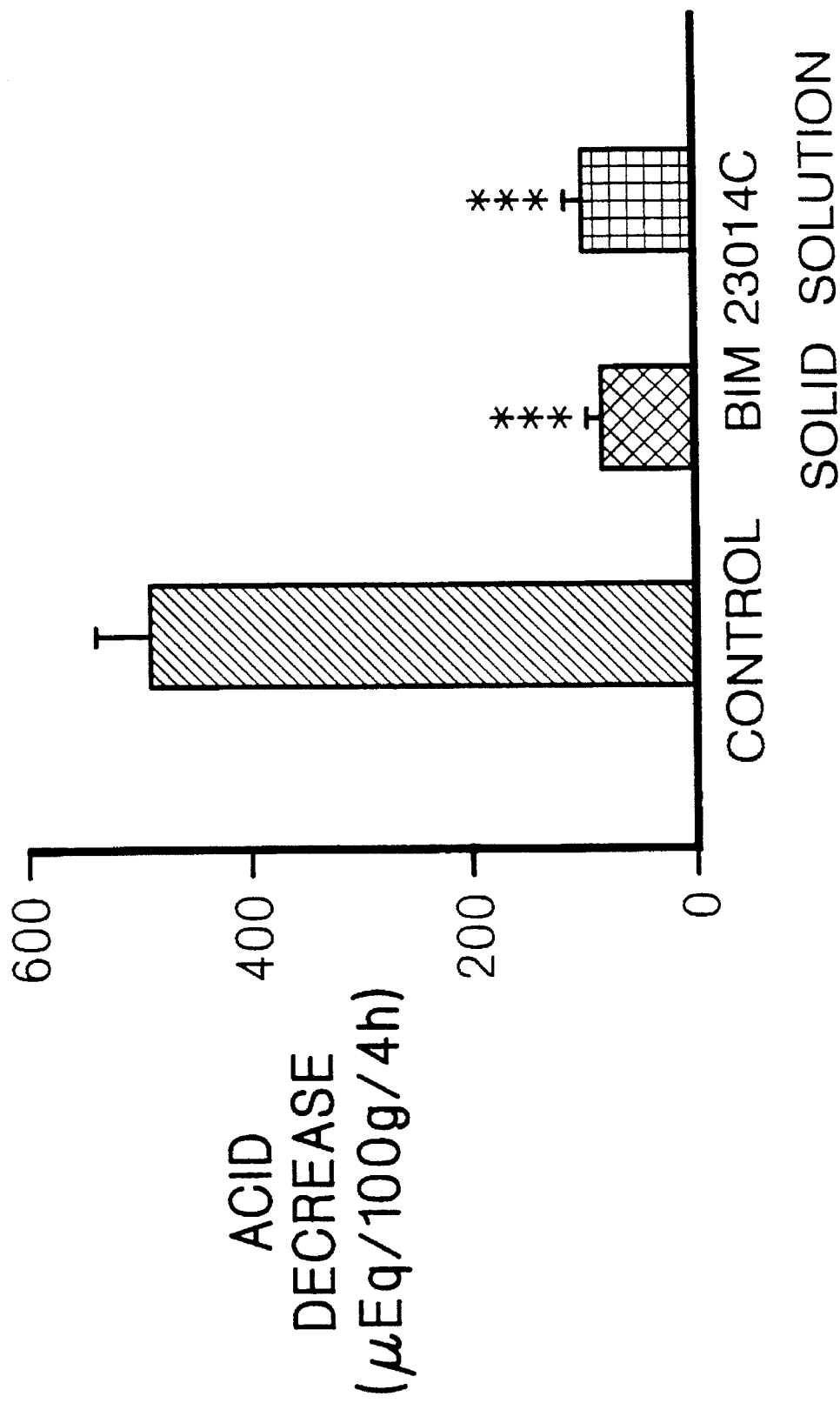
Figure 12C:
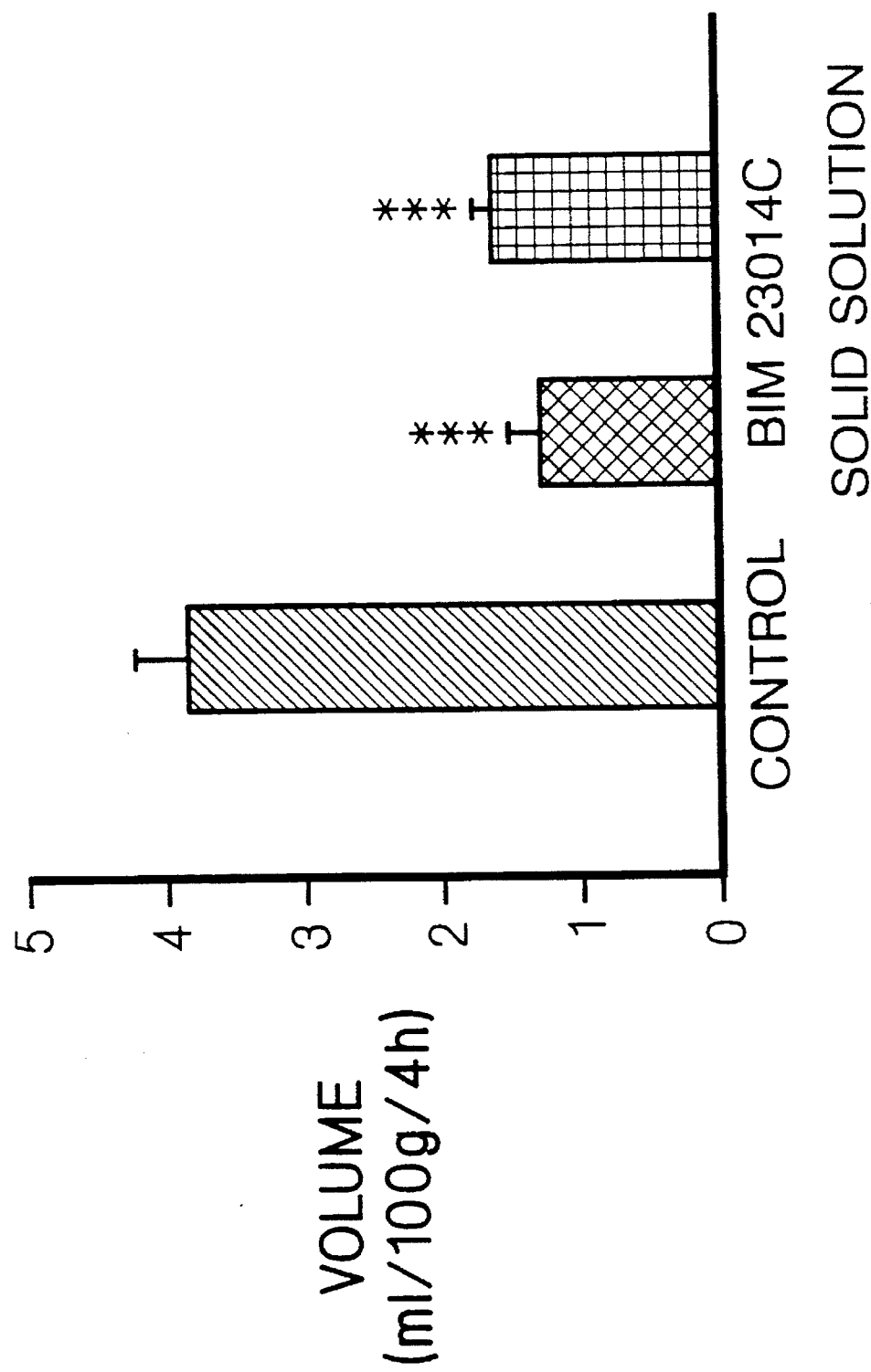

In an experiment in rats, the action of BIM-23014C on gastric secretion was determined for a solid 100% BIM-23104C formulation at a dosage of 50 µg/rat, a liquid BIM-23014C solution at a dosage of 50 µg/ml (1 ml injected into each rat), and a physiological serum control. The results show that in terms of acid concentration (FIG. 12A), decrease in acid (FIG. 12B), and acid volume (FIG. 12C), the solid and liquid solution formulations had essentially the same effect.

EXAMPLE 6

10% Hyaluronate, 5% POLOXAMER 188, 85% BIM-23014C

The above protocol was also performed by mixing 0.4065 g of Na hyaluronate, 0.2157 g of POLOXAMER® 188, and 7.215 g of water to form a gel. 0.280 g of this gel was added to 0.120 g of SOMATULINE® acetate. The mixture was weighed, kneaded, and extruded. The extrudate was cut and collected on glass slides, and dried under vacuum for 24 hours. The resulting 3.6 cm cylinders contained 0.648 mg of SOMATULINE®/cm (10% by weight Na hyaluronate, 5% POLOXAMER® 188, and 85% SOMATULINE® acetate). Thus, each cylinder contained 3.6 cm×0.648 mg/cm=2.33 mg of SOMATULINE®.

EXAMPLE 7

80% BIM-23014C, 20% Mannitol

The above protocol was also performed by mixing 1.00 g of mannitol and 9.0 g of water to form a solution. 0.14122 g of this solution was added to 0.0605 g of SOMATULINE® acetate. The mixture was weighed, kneaded, and extruded. The extrudate was cut and collected on glass slides, and dried under vacuum for 24 hours. The resulting 3.6 cm cylinders contained 1.22 mg of SOMATULINE®/cm (20% by weight mannitol and 80% SOMATULINE® acetate). Thus, each cylinder contained 3.6 cm×1.220 mg/cm=4.39 mg of SOMATULINE®.

EXAMPLE 8

90% BIM-23014C, 10% Sorbitol

The above protocol was also performed by mixing 1.0096 g of sorbitol and 19.0053 g of water to form a solution. 0.14 g of this solution was added to 0.06094 g of SOMATULINE® acetate. The mixture was weighed, kneaded, and extruded. The extrudate was cut and collected on glass slides, and dried under vacuum for 24 hours. The resulting 3.6 cm cylinders contained 0.644 mg of SOMATULINE®/cm (10% by weight sorbitol and 90% SOMATULINE® acetate). Thus, each cylinder contained 3.6 cm×0.644 mg/cm=2.31 mg of SOMATULINE®.

EXAMPLE 9

84% BIM-23014C, 16% Polysorbate 80

The above protocol was also performed by mixing 0.8 g of POLYSORBATE 80 and 9.2 g of water to form a solution. 0.14079 g of this solution was added to 0.06 g of SOMATULINE® acetate. The mixture was weighed, kneaded, and extruded. The extrudate was cut and collected on glass slides, and dried under vacuum for 24 hours. The resulting 3.6 cm cylinders contained 0.6459 mg of SOMATULINE®/cm (16% by weight POLYSORBATE 80 and 85% SOMATULINE® acetate). Thus, each cylinder contained 3.6 cm×0.6459 mg/cm=2.3 mg of SOMATULINE®.

EXAMPLE 10

84% BIM23014C, 16% Polyvinylpyrrolidone (PVP)

The above protocol was also performed by mixing 0.64 g of PVP and 7.37 of water to form a gel. 142 mg of this gel was added to 64 mg of SOMATULINE® acetate. The mixture was weighed, kneaded, and extruded. The extrudate was cut and collected on glass slides, and dried under vacuum for 24 hours. The resulting 3.6 cm cylinders contained 0.6207 mg of SOMATULINE®/cm (14% by weight PVP and 86% SOMATULINE® acetate). Thus, each cylinder contained 3.6 cm×0.6207 mg/cm=2.23 mg of SOMATULINE®.

EXAMPLE 11

85% BIM-23014C, 15% Sodium Hyaluronic Acid

The above protocol was performed by mixing 1.0 g of Na hyaluronic acid and 9.0 g of water. 0.24417 g of the resulting gel was added to 0.13864 g of the acetate salt of BIM-23014. The mixture was extruded through a 2.3 mm syringe (0.3 mm internal diameter needle) and cut. The resulting 3.6 cm cylinders had a dosage of 0.993 mg/cm (weight percentage 15% hyaluronic acid and 85% BIM-23014). Therefore, each 3.6 cm cylinder contained 3.57 mg of SOMATULINE®.

EXAMPLE 12

95.7% BIM-23014C, 4.3% Carboxy Methylcellulose

The above protocol was also performed by mixing 0.3 g of CMC and 9.7 g of water. 0.2095 g of the resulting gel was added to 0.13992 g of BIM-23014. The mixture was extruded through a 2.3 mm syringe (0.3 mm internal diameter needle) and cut. The resulting 3.6 cm cylinders had a dosage of 0.929 mg/cm (weight percentage 4.3% CMC and 95.7% BIM-23014). Thus, each 3.6 cm cylinder contained 3.34 mg of SOMATULINE®.

EXAMPLE 13

100% Anti-Platelet Activating Factor

The above protocol was performed by mixing 86 mg of water and 114 mg of synthetic anti-platelet activating factor (anti-PAF), 4,7,8,10-tetrahydro-1-methyl-6-(2-chlorphenyl)-9-(4-methoxyphenyl-thiocarbamoyl)-pyrrido-[4',3'-4,5]thieno[3,2-f]-1,2,4-triazolo[4,3-a]1,4-diazepine (BN 50730), or a natural anti-PAF, ginkgolide B (BN 52021). The mixture was extruded through a 2.3 mm syringe (0.3 internal diameter needle) and cut. The resulting cylinders had a dosage of 1.0 mg/1 cm.

Figure 13:
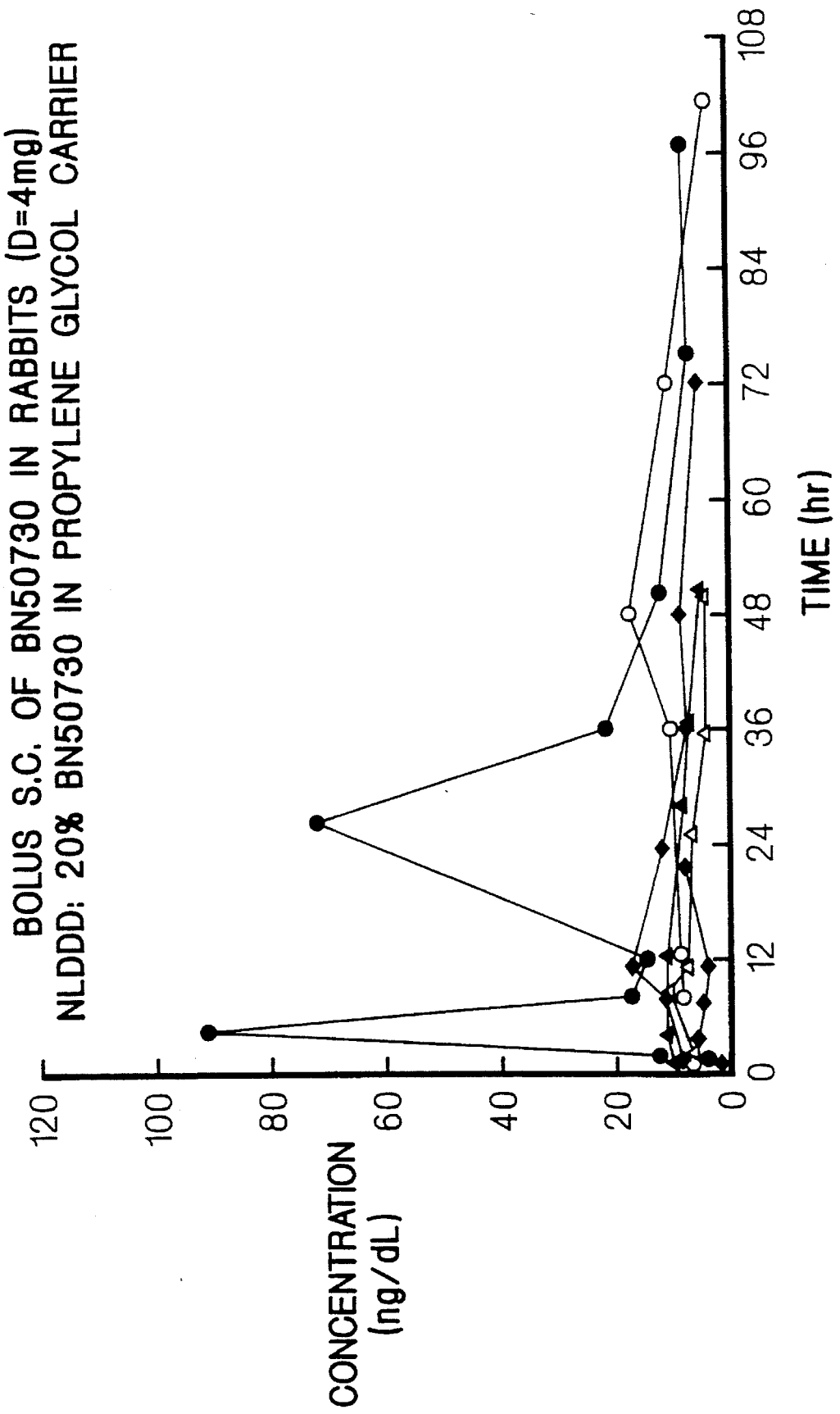
FIG. 13 is a graph of plasma levels in rats of a synthetic anti-platelet activating factor (anti-PAF)(BN 50730) injected subcutaneously.

These cylinders were injected subcutaneously into rabbits at a dosage of 2.0 mg/kg for a comparison study with BN 50730 mixed with propylene glycol. For this insoluble compound, the solid formulation provides an immediate effect in plasma. As shown in FIG. 13, a 4.0 mg dose of a paste of 20% BN 50730 in 80% propylene glycol injected subcutaneously into rabbits (n=5) provided a relatively constant concentration of about 10 ng/ml in the plasma over 48 to 96 hours (except for one rabbit that showed high peaks in concentration at 6 and 24 hours and then leveled off from 36 to 96 hours). This 10 ng/ml is a sufficient concentration for a pharmacological effect.

Figure 14:
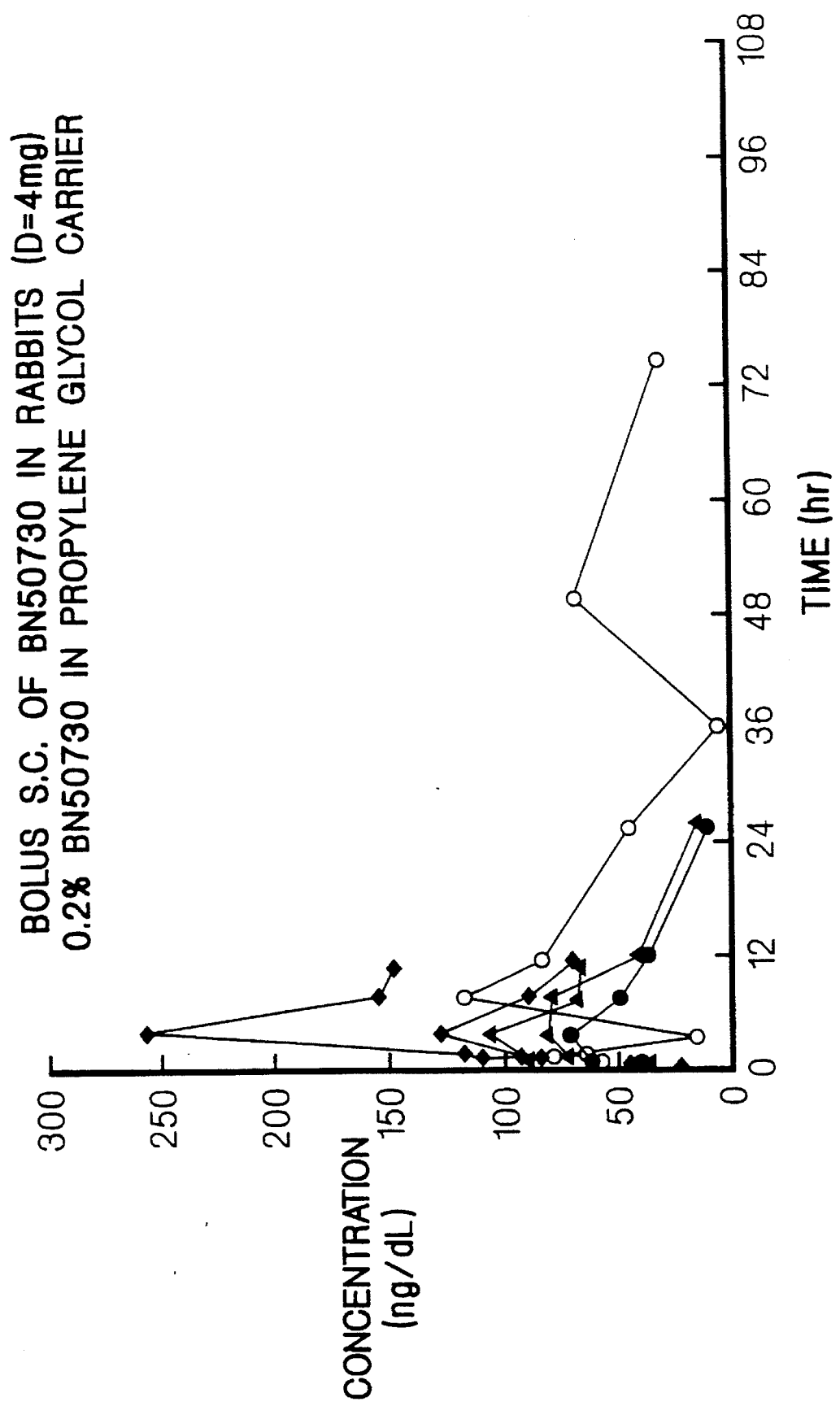
FIG. 14 is a graph of plasma levels in rats of a synthetic anti-platelet activating factor (anti-PAF)(BN 50730) injected subcutaneously as a liquid solution.

On the other hand, as shown in FIG. 14, a 4.0 mg dose of a 0.2% solution of BN 50730 in propylene glycol provided a consistently higher initial peak in plasma concentration with a rapid decline in concentration by 24 hours (except in one rabbit o, which was reinjected at 36 hours, and in which the concentration varied throughout a 72 hour period).

Figure 15:
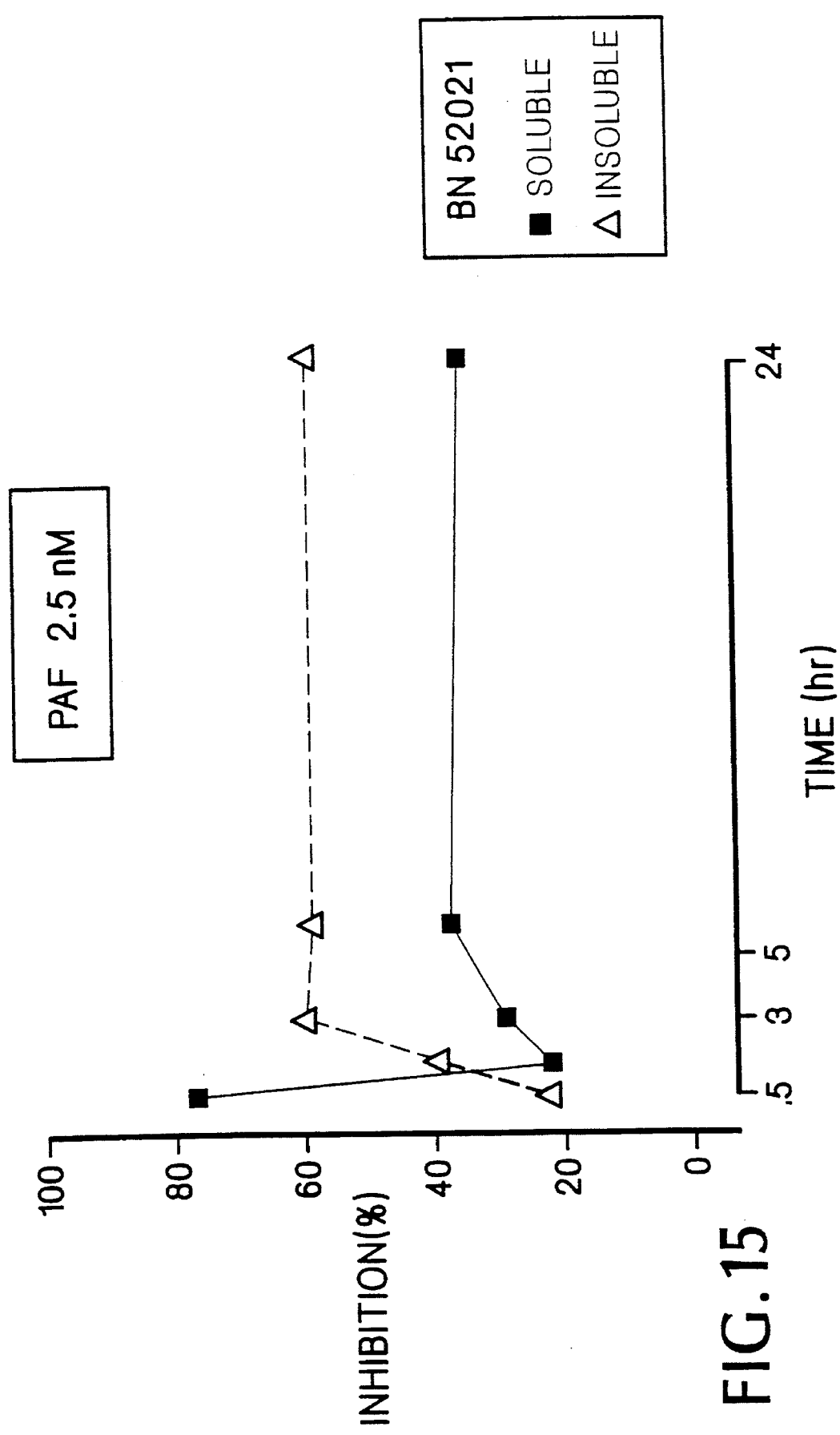
FIG. 15 is a graph showing the percent inhibition of platelet aggregation induced by 2.5 nM platelet activating factor (PAF) caused by both solid and standard liquid formulations of a natural anti-PAF, ginkgolide B (BN 52021).

The biological effect of BN 52021, i.e., inhibiting platelet aggregation induced by PAF, in an ex vivo rabbit test was comparable for the same dosage of drug in solution form (NaCl at a pH of 8.75, at a dosage of 0.5 ml/kg) and in the solid form (in which the drug was mixed with miglyol 812), and began at the same time. As shown in FIG. 15, at a concentration of 2.5 nM PAF, the anti-PAF drug BN 52021 in the liquid solution provided an initial peak of platelet aggregation inhibition at about 30 minutes that was higher than the inhibition due to the solid form, but the solid BN 52021 composition provided a higher overall inhibition of platelet aggregation than the liquid formulation from one hour on. Both formulations still had a significant inhibitory effect after 24 hours.

EXAMPLE 14

93% BN 52021, 7% Hyaluronate

The above protocol was performed by mixing 0.75 g of Na hyaluronate and 9.25 g of water. 0.18912 g of the resulting gel was added to 0.1885 g of BN 52021. The mixture was extruded through a 2.3 mm syringe (0.3 mm internal diameter needle) and cut. The resulting 2.3 cm cylinders had a dosage of 0.678 mg/cm of BN 52021 for a total of 1.56 mg per cylinder (weight percentage 7% hyaluronic acid and 93% BN 52021).

EXAMPLE 15

98% BN 52021, 2% Carboxy Methylcellulose

The above protocol was also performed by mixing 0.3 g of CMC and 9.7 g of water. 0.09347 g of the resulting gel was added to 0.12076 g of BN 52021. The mixture was extruded through a 2.3 mm syringe (0.3 mm internal diameter needle) and cut. The resulting 2.3 cm cylinders had a dosage of 0.998 mg/cm of BN 52021 for a total of 2.29 mg per cylinder (weight percentage 2% CMC and 98% BN-52021).

EXAMPLE 16

100% Tetracaine HCL

The above protocol was also performed by mixing 169.86 mg tetracaine HCL, a local anesthetic, and 92.24 mg of water. The mixture was extruded through a 2.3 mm syringe (0.5 mm internal diameter needle) and cut. The resulting cylinders were loaded into needles of 0.8 mm external diameter and the anesthetic effect was compared to a control solution formulation.

Figure 16:
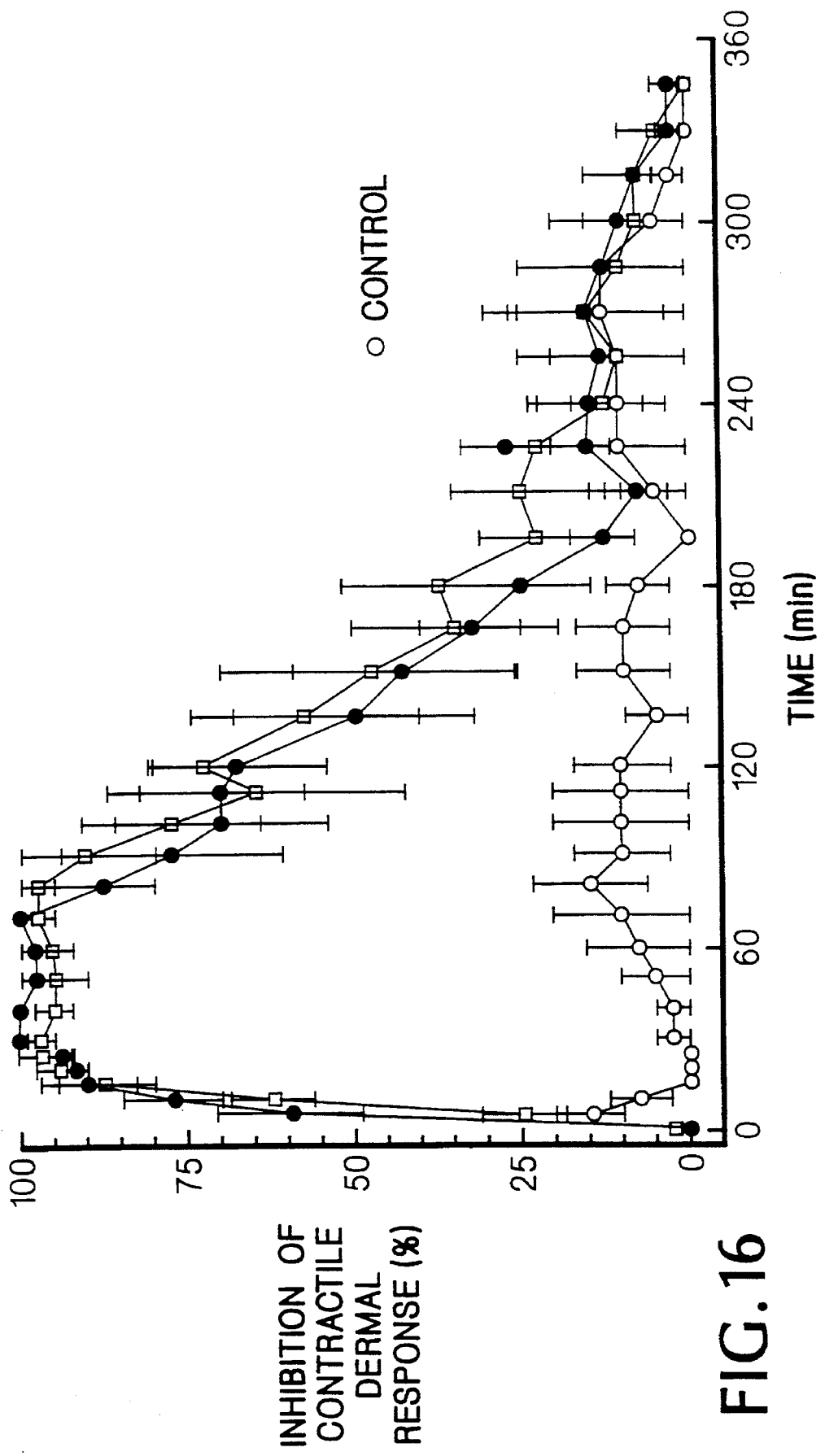
FIG. 16 is a graph showing the comparative dermal anaesthetic effect in rabbits of solid and liquid formulations of tetracaine versus a control.

The effect of this solid formulation was tested in a rabbit model of dermal contractibility caused by punch stimulation (10 punches in 10 seconds). Four male New Zealand rabbits were injected subcutaneously with tetracaine in solution (3.0 mg/0.2 ml) form (● in FIG. 16), tetracaine in powder (3.04 mg) form (□), and with physiological saline solution (o) in three randomized circles on the back (shaved) of each rabbit.

The measurement of dermal contractibility to the punch stimulation was performed under blind conditions before and after injection of the compounds at different time intervals: every 5 minutes (0–30 minutes), every 10 minutes (30–120 minutes), and every 15 minutes (120–345 minutes). The mean inhibition of dermal response (±S.E.M.) by the different treatments is summarized in the graph of FIG. 16, which shows no practical pharmacological differences in the effect profiles induced by the tetracaine solution and powder. This test with a drug powder reflects the bloodstream characteristics of a solid drug cylinder of this soluble drug.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications within the scope of the invention will be apparent to those skilled in the art to which the invention pertains.

What is claimed is:

1. An external, wearable device for the automatic, controlled administration of a solid drug composition to a patient comprising:

a housing;

a plunger located within said housing;

a dispensing tube attached to the outside of said housing, said tube being designed and sized to contain a solid drug composition consisting essentially of the drug and up to 50%, by weight, of a pharmaceutically acceptable carrier, wherein the solid drug has a diameter of less than about 0.8 millimeters;

an actuator arranged within said housing to move said plunger from said housing into said dispensing tube;

a controller that acts on said actuator to regulate the movement of said plunger through said housing and into said dispensing tube; and a power source arranged to provide energy to said actuator and said controller;

wherein said plunger is capable of moving the solid drug composition out of said dispensing tube at a controlled rate.

2. A device of claim 1, wherein said controller comprises an electrical motor, and said power source is a battery.

3. A device of claim 2, wherein said controller further comprises a microcomputer programmed with a predetermined delivery profile to provide said controlled rate of delivery.

4. A device of claim 1, wherein said actuator comprises two rotating wheels arranged to contact and move said plunger into said dispensing tube.

5. A device of claim 1, wherein said housing has a size of less than 3.0 cm and a thickness of less than 0.5 cm.

6. A method of automatically administering a drug to a patient according to a predetermined delivery profile comprising:

(a) obtaining a device of claim 1;

(b) loading a solid drug composition into said dispensing tube;

(c) inserting said dispensing tube into the patient;

(d) programming said controller of said device to cause said actuator to move said plunger through said dispensing tube according to a predetermined delivery profile;

(e) providing energy to said controller and said actuator to move said plunger within said dispensing tube to move the solid drug composition out of said dispensing tube and into the patient to deliver said drug to body fluids of the patient according to a predetermined delivery profile.

7. A method of claim 6, wherein said device is attached to the patient's skin with an adhesive.

8. A device of claim 1, wherein said dispensing tube is designed and sized to contain a cylindrical solid drug composition having a diameter of 0.1 to 0.8 millimeters.

* * * * *